(12) United States Patent
Helleday et al.

(10) Patent No.: US 7,351,701 B2
(45) Date of Patent: Apr. 1, 2008

(54) THERAPEUTIC COMPOUNDS

(75) Inventors: Thomas Helleday, Stockholm (SE); Nicola Curtin, Tyne and Wear (GB)

(73) Assignees: Cancer Research Technology Limited, London (GB); Pfizer, Inc., New York, NY (US)

( * ) Notice: Subject to any disclaimer, the term of this patent is extended or adjusted under 35 U.S.C. 154(b) by 62 days.

(21) Appl. No.: 10/898,653

(22) Filed: Jul. 23, 2004

(65) Prior Publication Data

US 2005/0143370 A1    Jun. 30, 2005

(51) Int. Cl.
  *A61P 35/00* (2006.01)
(52) U.S. Cl. .................. 514/212.04; 514/220
(58) Field of Classification Search ........... 540/498, 540/520; 514/212.06, 220, 212.04
  See application file for complete search history.

(56) References Cited

U.S. PATENT DOCUMENTS

| 6,495,541 | B1 * | 12/2002 | Webber et al. ......... 514/212.06 |
| 6,548,494 | B1 * | 4/2003 | Webber et al. ............. 514/220 |
| 2004/0248879 | A1 * | 12/2004 | Canan-Koch et al. ....... 514/215 |
| 2005/0059663 | A1 | 3/2005 | Martin et al. |
| 2005/0227919 | A1 | 10/2005 | Ashworth et al. |
| 2006/0074073 | A1 | 4/2006 | Steinfeldt et al. |

FOREIGN PATENT DOCUMENTS

| WO | 0042040 | A1 | 7/2000 |
| WO | 0116136 | A2 | 3/2001 |
| WO | 2004087713 | A1 | 10/2004 |
| WO | 2005012305 | A2 | 2/2005 |
| WO | 2005012524 | A1 | 2/2005 |

OTHER PUBLICATIONS

Bryant, et al., Specific killing of BRCA2-deficient tumours with inhibitors of poly(ADP-ribose) polymerase, Nature, Apr. 14, 2005, 913-917, vol. 434.

Canan Koch, et al., Novel Tricyclic Poly(ADP-ribose) Polymerase-1 Inhibitors with Potent Anticancer Chemopotentiating Activity: Design, Synthesis, and X-ray Cocrystal Structure, J. Med. Chem., 2002, 4961-4974, vol. 45, No. 23.

Easton, et al., Cancer Risks in BRCA2 Mutation Carriers, J. Natl. Cancer Inst., 1999, 1310-1316, vol. 91, No. 15.

Farmer, et al., Targeting the DNA repair defect in BRCA mutant cells as a therapeutic strategy, Nature, Apr. 14, 2005, 917-921, vol. 434.

Friedenson, et al., BRCA1 and BRCA2 Pathways and the Risk of Cancers Other Than Breast or Ovarian, Medscape General Medicine, 2005, 7(2):60.

Lakhani, et al., The Pathology of Familial Breast Cancer: Predictive Value of Immunohistochemical Markers Estrogen Receptor, Progesterone Receptor, HER-2, and p53 in Patients With Mutations in BRCA1 and BRCA2, Journal of Clinical Oncology, May 1, 2002, 2310-2318, vol. 20, No. 9.

Quinn, et al., BRCA1 Functions as a Different Modulator of Chemotherapy-induced Apoptosis, Cancer Research, Oct. 1, 2003, 6221-6228, vol. 63.

Taron, et al., BRCA1 mRNA expression levels as an indicator of chemoresistance in lung cancer, Human Molecular Genetics, 2004, 2443-2449, vol. 13, No. 20.

Tutt, et al., The relationship between the roles of BRCA genes in DNA repair and cancer predisposition, Trends in Molecular Medicine, Dec. 2002, 571-576, vol. 8, No. 12.

Venkitaraman, A. R., Cancer Susceptibility and the Functions of BRCA1 and BRCA2, Cell, Jan. 25, 2002, 171-182, vol. 108.

PCT International Search Report for PCT/GB2004/003183 (WO 2005/012305).

PCT Written Opinion of the International Searching Authority for PCT/GB2004/003183 (WO 2005/012305).

* cited by examiner

*Primary Examiner*—Bruck Kifle
(74) *Attorney, Agent, or Firm*—Notaro & Michalos P.C.

(57) ABSTRACT

The invention relates to trycyclic lactam indole derivatives and triacyclic lactam benzimodole derivatives and their use in inhibiting the activity of PARP enzyme. The invention also relates to the use of these compounds in the preparation of medicaments.

6 Claims, 8 Drawing Sheets

SEQUENCE LISTING

```
<160> NUMBER OF SEQ ID NOS: 6

<210> SEQ ID NO 1
<211> LENGTH: 5468
<212> TYPE: DNA
<213> ORGANISM: Homo Sapien

<400> SEQUENCE: 1
cgcccgccca gccccggggg cagggaaagc ctaaattacg gaattaccgc gagcaaggag      60
cgcggaatcg gggagcgtcc ggagctagct ggatcctcta ggcaggatgg tgatgggaat    120
ctttgcaaat tgtatcttct gtttgaaagt gaagtactta cctcagcagc agaagaaaaa    180
gctacaaact gacattaagg aaaatggcgg aaagttttcc ttttcgttaa atcctcagtg    240
cacacatata atcttagata atgctgatgt tctgagtcag taccaactga attctatcca    300
aaagaaccac gttcatattg caaacccaga ttttatatgg aaatctatca gagaaaagag    360
actcttggat gtaaagaatt atgatcctta taagccctg gacatcacac cacctcctga    420
tcagaaggcg agcagttctg aagtgaaaac agaaggtcta tgcccggaca gtgccacaga    480
ggaggaagac actgtggaac tcactgagtt tggtatgcag aatgttgaaa ttcctcatct    540
tcctcaagat tttgaagttg caaatataa caccttggag aaagtgggaa tggagggagg    600
ccaggaagct gtggtggtgg agcttcagtg ttcgcgggac tccagggact gtcctttcct    660
gatatcctca cacttcctcc tggatgatgg catggagact agaagacagt ttgctataaa    720
gaaaacctct gaagatgcaa gtgaatactt tgaaaattac attgaagaac tgaagaaaca    780
```

```
aggatttcta ctaagagaac atttcacacc tgaagcaacc caattagcat ctgaacaatt    840
gcaagcattg cttttggagg aagtcatgaa ttcaagcact ctgagccaag aggtgagcga    900
tttagtagag atgatttggg cagaggccct gggccacctg aacacatgc ttctcaagcc    960 agtgaacagg attagcctca acgatgtgag caaggcagag gggattctcc ttctagtaaa    1020
ggcagcactg aaaaatggag aaacagcaga gcaattgcaa aagatgatga cagagtttta    1080
cagactgata cctcacaaag gcacaatgcc caaagaagtg aacctgggac tattggctaa    1140
gaaagcagac ctctgccagc taataagaga catggttaat gtctgtgaaa ctaatttgtc    1200
caaacccaac ccaccatccc tggccaaata ccgagctttg aggtgcaaaa ttgagcatgt    1260
tgaacagaat actgaagaat ttctcagggt tagaaaagag gttttgcaga atcatcacag    1320
taagagccca gtggatgtct tgcagatatt tagagttggc agagtgaatg aaaccacaga    1380 gttttttgagc aaacttggta atgtgaggcc cttgttgcat ggttctcctg tacaaaacat    1440
cgtgggaatc ttgtgtcgag ggttgctttt acccaaagta gtggaagatc gtggtgtgca    1500
aagaacagac gtcggaaacc ttggaagtgg gatttatttc agtgattcgc tcagtacaag    1560
tatcaagtac tcacacccgg gagagacaga tggcaccaga ctcctgctca tttgtgacgt    1620
agccctcgga aagtgtatgg acttacatga aaggactttt tccttaactg aagcaccacc    1680
aggctacgac agtgtgcatg gagtttcaca acagcctct gtcaccacag actttgagga    1740
tgatgaattt gttgtctata aaccaatca ggttaaaatg aaatatatta ttaaattttc    1800
catgcctgga gatcagataa aggactttca tcctagtgat catactgaat tagaggaata    1860
cagacctgag ttttcaaatt tttcaaaggt tgaagattac cagttaccag atgccaaaac    1920
ttccagcagc accaaggccg gcctccagga tgcttctggg aacttggttc ctctggagga    1980
tgtccacatc aaagggagaa tcatagacac tgtagcccag gtcattgttt ttcagacata    2040
cacaaataaa agtcacgtgc ccattgaggc aaaatatatc tttcctttgg atgacaaggc    2100
cgctgtgtgt ggcttcgaag ccttcatcaa tgggaagcac atagttggag agattaaaga    2160
gaaggaagaa gcccagcaag agtacctaga agccgtgacc cagggccatg gcgcttacct    2220
gatgagtcag gatgctccgg acgttttac tgtaagtgtt ggaaacttac cccctaaggc    2280
taaggttctt ataaaaatta cctacatcac agaactcagc atcctgggca ctgttggtgt    2340 cttttttcatg cccgccaccg tagcaccctg gcaacaggac aaggcttga atgaaaacct    2400 tcaggataca gtagagaaga tttgtataaa agaaatagga acaaagcaaa gcttctcttt    2460
gactatgtct attgagatgc cgtacgtgat tgaattcatt ttcagtgata ctcatgaact    2520
gaaacaaaag cgcacagact gcaaagctgt cattagcacc atggaaggca gctccttaga    2580
cagcagtgga ttttctctcc acatcggttt gtctgctgcc tatctcccaa gaatgtgggt    2640
tgaaaaacat ccagaaaaag aaagcgaggc ttgcatgctt gtctttcaac ccgatctcga    2700
tgtcgacctc cctgacctag ccaatgagag cgaagtgatt atttgtcttg actgctccag    2760
ttccatggag ggtgtgacat tcttgcaagc caaggaaatc gccttgcatg cgctgtcctt    2820
ggtgggtgag aagcagaaag taaatattat ccagttcggc acaggttaca aggagctatt    2880
ttcgtatcct aagcatatca caagcaatac cgcggcagca gagttcatca tgtctgccac    2940
acctaccatg gggaacacag acttctggaa aacactccga tatcttagct tattgtaccc    3000
tgctcgaggg tcacggaaca tcctcctggt gtctgatggg cacctccagg atgagagcct    3060
gacattacag ctcgtgaaga ggagccgcc gcacaccagg ttattcgcct gcggtatcgg    3120
```

```
ttctacagca aatcgtcacg tcttaaggat tttgtcccag tgtggtgccg gagtatttga   3180
atattttaat gcaaaatcca agcatagttg gagaaaacag atagaagacc aaatgaccag   3240
gctatgttct ccgagttgcc actctgtctc cgtcaaatgg cagcaactca atccagatgc   3300
gcccgaggcc ctgcaggccc cagcccaggt gccatccttg tttcgcaatg atcgactcct   3360
tgtctatgga ttcattcctc actgcacaca ggcaactctg tgtgcactaa ttcaagagaa   3420
agaattttgt acaatggtgt cgactactga gcttcagaag acaactggaa ctatgatcca   3480
caagctggca gcccgagctc taatcagaga ttatgaagat ggcattcttc acgaaaatga   3540
aaccagtcat gagatgaaaa acaaaacctt gaaatctctg attattaaac tcagtaaaga   3600
aaactctctc ataacacaat ttacaagctt tgtggcagtt gagaaagggg atgagaatga   3660
gtcacctttt cctgatattc caaaagtttc tgaacttatt gccaagaag atgtagactt    3720
cctgccctac atgagctggc aggggaacc ccaagaagcc gtcaggaacc agtctctttt    3780
agcatcctct gagtggccag aattacgttt atccaaacga aaacatagga aaattccatt   3840
ttccaaaaga aaaatggaat tatctcagcc agaagtttct gaagattttg aagaggatgc   3900
cttaggtgta ctaccagctt tcacatcaaa tttggaacgt ggacgtgtgg aaaagctatt   3960
ggatttaagt tggacagagt catgtaaacc aacagcaact gaaccactat ttaagaaagt   4020
cagtccatgg gaaacatcta cttctagctt ttttcctatt ttggctccgg ccgttggttc   4080
ctatcttacc ccgactaccc gcgctcacag tcctgcttcc ttgtcttttg cctcatatcg   4140
tcaggtagct agtttcggtt cagctgctcc tcccagacag tttgatgcat ctcaattcag   4200
ccaaggccct gtgcctggca cttgtgctga ctggatccca cagtcggcgt cttgtcccac   4260
aggacctccc cagaacccac cttctgcacc ctattgtggc attgtttttt cagggagctc   4320
attaagctct gcacagtctg ctccactgca acatcctgga ggctttacta ccaggccttc   4380
tgctggcacc ttccctgagc tggattctcc ccagcttcat ttctctcttc ctacagaccc   4440
tgatcccatc agaggttttg ggtcttatca tccctctgct tactctcctt ttcattttca   4500
accttccgca gcctctttga ctgccaacct taggctgcca atggcctctg ctttacctga   4560
ggctctttgc agtcagtccc ggactacccc agtagatctc tgtcttctag aagaatcagt   4620
aggcagtctc gaaggaagtc gatgtcctgt ctttgctttt caaagttctg acacagaaag   4680
tgatgagcta tcagaagtac ttcaagacag ctgcttttta caaataaaat gtgatacaaa   4740
agatgacagt atcccgtgct ttctggaagt aaaagaagag gatgaaatag tgtgcacaca   4800
acactggcag gatgctgtgc cttggacaga actcctcagt ctacagacag aggatggctt   4860
ctggaaactt acaccagaac tgggacttat attaaatctt aatacaaatg gtttgcacag   4920
cttttcttaaa caaaaaggca ttcaatctct aggtgtaaaa ggaagagaat gtctcctgga   4980
cctaattgcc acaatgctgg tactacagtt tattcgcacc aggttggaaa agagggaat    5040
agtgttcaaa tcactgatga aaatggatga cccttctatt tccaggaata ttccctgggc   5100
ttttgaggca ataaagcaag caagtgaatg ggtaagaaga actgaaggac agtacccatc   5160
tatctgccca cggcttgaac tggggaacga ctgggactct gccaccaagc agttgctggg   5220
actccagccc ataagcactg tgtcccctct tcatagagtc ctccattaca gtcaaggcta   5280
agtcaaatga aactgaattt taaacttttt gcatgcttct atgtagaaaa taatcaaatg   5340
ataatagata cttataatga aacttcatta aggtttcatt cagtgtagca attactgtct   5400
ttaaaaatta agtggaagaa gaattacttt aatcaactaa caagcaataa taaaatgaaa   5460
cttaaaat                                                           5468
```

<210> SEQ ID NO 2
<211> LENGTH: 1910
<212> TYPE: DNA
<213> ORGANISM: Homo Sapien

<400> SEQUENCE: 2

| | | | | | |
|---|---|---|---|---|---|
| ctagaattca | gcggccgctg | aattctaggc | ggcgcggcgg | cgacggagca | ccggcggcgg | 60 |
| cagggcgaga | gcattaaatg | aaagcaaaag | agttaataat | ggcaacacgg | ctccagaaga | 120 |
| ctcttcccct | gccaagaaaa | ctcgtagatg | ccagagacag | gagtcgaaaa | agatgcctgt | 180 |
| ggctggagga | aaagctaata | aggacaggac | agaagacaag | caagatggta | tgccaggaag | 240 |
| gtcatgggcc | agcaaaaggg | tctctgaatc | tgtgaaggcc | ttgctgttaa | agggcaaagc | 300 |
| tcctgtggac | ccagagtgta | cagccaaggt | ggggaaggct | catgtgtatt | gtgaaggaaa | 360 |
| tgatgtctat | gatgtcatgc | taaatcagac | caatctccag | ttcaacaaca | acaagtacta | 420 |
| tctgattcag | ctattagaag | atgatgccca | gaggaacttc | agtgtttgga | tgagatgggg | 480 |
| ccgagttggg | aaaatgggac | agcacagcct | ggtggcttgt | tcaggcaatc | tcaacaaggc | 540 |
| caaggaaatc | tttcagaaga | aattccttga | caaaacgaaa | aacaattggg | aagatcgaga | 600 |
| aaagtttgag | aaggtgcctg | aaaaatatga | tatgctacag | atggactatg | ccaccaatac | 660 |
| tcaggatgaa | gaggaaacaa | aaaagagga | atctcttaaa | tctcccttga | agccagagtc | 720 |
| acagctagat | cttcgggtac | aggagttaat | aaagttgatc | tgtaatgttc | aggccatgga | 780 |
| agaaatgatg | atgaaatga | agtataatac | caagaaagcc | ccacttggga | agctgacagt | 840 |
| ggcacaaatc | aaggcaggtt | accagtctct | taagaagatt | gaggattgta | ttcgggctgg | 900 |
| ccagcatgga | cgagctctca | tggaagcatg | caatgaattc | tacaccagga | ttccgcatga | 960 |
| ctttggactc | cgtactcctc | cactaatccg | gacacagaag | gaactgtcag | aaaaaataca | 1020 |
| attactagag | gctttgggag | acattgaaat | tgctattaag | ctggtgaaaa | cagagctaca | 1080 |
| aagcccagaa | cacccattgg | accaacacta | tagaaaccta | cattgtgcct | tgcgccccct | 1140 |
| tgaccatgaa | agttacgagt | tcaaagtgat | ttcccagtac | ctacaatcta | cccatgctcc | 1200 |
| cacacacagc | gactatacca | tgaccttgct | ggatttgttt | gaagtggaga | aggatggtga | 1260 |
| gaaagaagcc | ttcagagagg | accttcataa | caggatgctt | ctatggcatg | gttccaggat | 1320 |
| gagtaactgg | gtgggaatct | tgagccatgg | gcttcgaatt | gcccaccctg | aagctcccat | 1380 |
| cacaggttac | atgtttggga | aaggaatcta | ctttgctgac | atgtcttcca | agagtgccaa | 1440 |
| ttactgcttt | gcctctcgcc | taaagaatac | aggactgctg | ctcttatcag | aggtagctct | 1500 |
| aggtcagtgt | aatgaactac | tagaggccaa | tcctaaggcc | gaaggattgc | ttcaaggtaa | 1560 |
| acatagcacc | aaggggctgg | gcaagatggc | tcccagttct | gcccacttcg | tcaccctgaa | 1620 |
| tgggagtaca | gtgccattag | gaccagcaag | tgacacagga | attctgaatc | cagatggtta | 1680 |
| taccctcaac | tacaatgaat | atattgtata | taaccccaac | caggtccgta | tgcggtacct | 1740 |
| tttaaaggtt | cagtttaatt | tccttcagct | gtggtgaatg | ttgatcttaa | ataaaccaga | 1800 |
| gatctgatct | tcaagcaaga | aaataagcag | tgttgtactt | gtgaattttg | tgatatttta | 1860 |
| tgtaataaaa | actgtacagg | tctaaaaaaa | aaaaaaaaa | aaaaaaaaa | | 1910 |

<210> SEQ ID NO 3
<211> LENGTH: 2263
<212> TYPE: DNA
<213> ORGANISM: Homo Sapien

<400> SEQUENCE: 3

```
tgggactggt cgcctgactc ggcctgcccc agcctctgct tcaccccact ggtggccaaa      60
tagccgatgt ctaatccccc acacaagctc atcccggcc tctgggattg ttgggaattc     120
tctccctaat tcacgcctga ggctcatgga gagttgctag acctgggact gccctgggag    180
gcgcacacaa ccaggccggg tggcagccag gacctctccc atgtccctgc ttttcttggc    240
catggctcca aagccgaagc cctgggtaca gactgagggc cctgagaaga agaagggccg    300
gcaggcagga agggaggagg accccttccg ctccaccgct gaggccctca aggccatacc    360
cgcagagaag cgcataatcc gcgtggatcc aacatgtcca ctcagcagca accccgggac    420
ccaggtgtat gaggactaca actgcaccct gaaccagacc aacatcgaga caacaacaa     480
caagttctac atcatccagc tgctccaaga cagcaaccgc ttcttcacct gctgaaccg     540
ctggggccgt gtgggagagg tcggccagtc aaagatcaac cacttcacaa ggctagaaga    600
tgcaaagaag gactttgaga gaaatttcg ggaaaagacc aagaacaact gggcagagcg     660
ggaccacttt gtgtctcacc cgggcaagta cacacttatc gaagtacagg cagaggatga    720
ggcccaggaa gctgtggtga aggtggacag aggcccagtg aggactgtga ctaagcgggt    780
gcagccctgc tccctggacc cagccacgca gaagctcatc actaacatct tcagcaagga    840
gatgttcaag aacaccatgg ccctcatgga cctggatgtg aagaagatgc ccctgggaaa    900
gctgagcaag caacagattg cacggggttt cgaggccttg gaggcgctgg aggaggccct    960
gaaaggcccc acgatggtg ccaaagcct ggaggagctg tcctcacact tttacaccgt     1020
catcccgcac aacttcggcc acagccagcc cccgcccatc aattcccctg agcttctgca    1080
ggccaagaag gacatgctgc tggtgctggc ggacatcgag ctggcccagg ccctgcaggc    1140
agtctctgag caggagaaga cggtggagga ggtgccacac ccctggacc gagactacca     1200
gcttctcaag tgccagctgc agctgctaga ctctggagca cctgagtaca aggtgataca    1260
gacctactta gaacagactg gcagcaacca caggtgccct acacttcaac acatctggaa    1320
agtaaaccaa gaaggggagg aagacagatt ccaggcccac tccaaactgg gtaatcggaa    1380
gctgctgtgg catggcacca acatggccgt ggtggccgcc atcctcacta gtgggctccg    1440
catcatgcca cattctggtg ggcgtgttgg caagggcatc tactttgcct cagagaacag    1500
caagtcagct ggatatgtta ttggcatgaa gtgtggggcc caccatgtcg gctacatgtt    1560
cctgggtgag gtggccctgg gcagagagca ccatatcaac acggacaacc ccagcttgaa    1620
gagcccacct cctggcttcg acagtgtcat tgcccgaggc cacaccgagc ctgatccgac    1680
ccaggacact gagttggagc tggatggcca gcaagtggtg gtgccccagg ccagcctgt     1740
gccctgccca gagttcagca gctccacatt ctccagagc gagtacctca tctaccagga    1800
gagccagtgt cgcctgcgct acctgctgga ggtccacctc tgagtgcccg ccctgtcccc    1860
cggggtcctg caaggctgga ctgtgatctt caatcatcct gcccatctct ggtaccccta    1920
tatcactcct tttttcaag aatacaatac gttgttgtta actatagtca ccatgctgta     1980
caagatccct gaacttatgc ctcctaactg aaatttgta ttctttgaca catctgccca     2040
gtccctctcc tcccagccca tggtaaccag catttgactc tttacttgta taagggcagc    2100
ttttataggt tccacatgta agtgagatca tgcagtgttt gtctttctgt gcctggctta    2160
tttcactcag cataatgtgc accgggttca cccatgtttt cataaatgac aagatttcct    2220
cctttaaaaa aaaaaaaaaa aaaaaaaaaa aaaaaaaaaa aaa                       2263
```

<210> SEQ ID NO 4
<211> LENGTH: 4491
<212> TYPE: DNA
<213> ORGANISM: Homo Sapien

<400> SEQUENCE: 4

| | | | | | | |
|---|---|---|---|---|---|---|
| cgaagatggc | ggcgtcgcgt | cgctctcagc | atcatcacca | ccatcatcaa | caacagctcc | 60 |
| agcccgcccc | aggggcttca | gcgccgccgc | cgccacctcc | tcccccactc | agccctggcc | 120 |
| tggccccggg | gaccacccca | gcctctccca | cggccagcgg | cctggccccc | ttcgcctccc | 180 |
| cgcggcacgg | cctagcgctg | ccggaggggg | atggcagtcg | ggatccgccc | gacaggcccc | 240 |
| gatccccgga | cccggttgac | ggtaccagct | gttgcagtac | caccagcaca | atctgtaccg | 300 |
| tcgccgccgc | tcccgtggtc | ccagcggttt | ctacttcatc | tgccgctggg | gtcgctccca | 360 |
| acccagccgg | cagtggcagt | aacaattcac | cgtcgtcctc | ttcttccccg | acttcttcct | 420 |
| catcttcctc | tccatcctcc | cctggatcga | gcttggcgga | gagccccgag | gcggccggag | 480 |
| ttagcagcac | agcaccactg | gggcctgggg | cagcaggacc | tgggacaggg | gtcccagcag | 540 |
| tgagcggggc | cctacgggaa | ctgctggagg | cctgtcgcaa | tggggacgtg | tcccgggtaa | 600 |
| agaggctggt | ggacgcggca | aacgtaaatg | caaaggacat | ggccggccgg | aagtcttctc | 660 |
| ccctgcactt | cgctgcaggt | tttggaagga | aggatgttgt | agaacactta | ctacagatgg | 720 |
| gtgctaatgt | ccacgctcgt | gatgatggag | gtctcatccc | gcttcataat | gcctgttctt | 780 |
| ttggccatgc | tgaggttgtg | agtctgttat | tgtgccaagg | agctgatcca | aatgccaggg | 840 |
| ataactggaa | ctatacacct | ctgcatgaag | ctgctattaa | agggaagatc | gatgtgtgca | 900 |
| ttgtgctgct | gcagcacgga | gctgacccaa | acattcggaa | cactgatggg | aaatcagccc | 960 |
| tggacctggc | agatccttca | gcaaaagctg | tccttacagg | tgaatacaag | aaagacgaac | 1020 |
| tcctagaagc | tgctaggagt | ggtaatgaag | aaaaactaat | ggctttactg | actcctctaa | 1080 |
| atgtgaattg | ccatgcaagt | gatgggcgaa | agtcgactcc | tttacatcta | gcagcgggct | 1140 |
| acaacagagt | tcgaatagtt | cagcttcttc | ttcagcatgg | tgctgatgtt | catgcaaaag | 1200 |
| acaaaggtgg | acttgtgcct | cttcataatg | catgttcata | tggacattat | gaagtcacag | 1260 |
| aactgctact | aaagcatgga | gcttgtgtta | atgccatgga | tctctggcag | tttactccac | 1320 |
| tgcacgaggc | tgcttccaag | aaccgtgtag | aagtctgctc | tttgttactt | agccatggcg | 1380 |
| ctgatcctac | gttagtcaac | tgccatggca | aaagtgctgt | ggatatggct | ccaactccgg | 1440 |
| agcttaggga | gagattgact | tatgaattta | aaggtcattc | tttactacaa | gcagccagag | 1500 |
| aagcagactt | agctaaagtt | aaaaaaacac | tcgctctgga | aatcattaat | ttcaaacaac | 1560 |
| cgcagtctca | tgaaacagca | ctgcactgtg | ctgtggcctc | tctgcatccc | aaacgtaaac | 1620 |
| aagtgacaga | attgttactt | agaaaaggag | caaatgttaa | tgaaaaaaat | aaagatttca | 1680 |
| tgactcccct | gcatgttgca | gccgaaagag | cccataatga | tgtcatggaa | gttctgcata | 1740 |
| agcatggcgc | caagatgaat | gcactggaca | cccttggtca | gactgctttg | catagagccg | 1800 |
| ccctagcagg | ccacctgcag | acctgccgcc | tcctgctgag | ttacggctct | gacccctcca | 1860 |
| tcatctcctt | acaaggcttc | acagcagcac | agatgggcaa | tgaagcagtg | cagcagattc | 1920 |
| tgagtgtgag | ttacggctct | gacccctcca | tcatctcctt | acaaggcttc | acagcagcac | 1980 |
| agatgggcaa | tgaagcagtg | cagcagattc | tgagtggtca | ttcgtagata | gtgatcattc | 2040 |
| tacttcagcc | ttaatggtga | tcttgagacg | ggaagattta | gaaggaaatc | tatccagcat | 2100 |
| gtcttcactg | tcaacatgaa | gagtacacct | atacgtactc | ctgatgttga | ttatcgactc | 2160 |

-continued

```
ttagaggcat ctaaagctgg agacttggaa actgtgaagc aactttgcag ctctcaaaat    2220
gtgaattgta gagacttaga gggccggcat tccacgccct tacacttcgc agcaggctac    2280
aacagagtac acctatacgt acttctgatg ttgattatcg actcttagag gcatctaaag    2340
ctggagactt ggaaactgtg aagcaacttt gcagctctca aaatgtgaat tgtagagact    2400
tagagggccg gcattccacg cccttacact tcgcagcagg ctacaaccgc gtgtctgttg    2460
tagagtacct gctacaccac ggtgccgatg tccatgccaa agacaagggt ggcttggtgc    2520
cccttcataa tgcctgttca tatggacact atgaggtggc tgagctttta gtaaggcatg    2580
gggcttctgt caatgtggcg gacttatgga aatttacccc tctccatgaa gcagcagcta    2640
aaggaaagta tgaaatctgc aagctccttt taaaacatgg agcagatcca actaaaaaga    2700
acagagatgg aaatacacct ttggatttgg taaaggaagg agacacagat attcaggact    2760
tactgaaagg ggatgctgct ttgttggatg ctgccaagaa gggctgcctg caagagtgc    2820
agaagctctg tacccagag aatatcaact gcagagacac ccagggcaga aattcaaccc    2880
ctctgcacct ggcagcaggc tataataacc tggaagtagc tgaatatctt ctagagcatg    2940
gagctgatgt taatgcccag acaagggtg gtttaattcc tcttcataat gcggcatctt    3000
atgggcatgt tgacatagcg gctttattga taaaatacaa cacgtgtgta aatgcaacag    3060
ataagtgggc gtttactccc ctccatgaag cagcccagaa aggaaggacg cagctgtgcg    3120
ccctcctcct agcgcatggt gcagacccca ccatgaagaa ccaggaaggc cagacgcctc    3180
tggatctggc aacagctgac gatatcgag cttgctgat agatgccatg cccccagagg    3240
ccttacctac ctgtttttaaa cctcaggcta ctgtagtgag tgcctctctg atctcaccag    3300
catccacccc ctcctgcctc tcggctgcca gcagcataga caacctcact ggcccttag    3360
cagagttggc cgtaggagga gcctccaatg caggggatgg cgccgcggga acagaaagga    3420
aggaaggaga agttgctggt cttgacatga atatcagcca atttctaaaa gccttggcc    3480
ttgaacacct tcgggatatc tttgaaacag aacagattac actagatgtg ttggctgata    3540
tgggtcatga agagttgaaa gaaataggca tcaatgcata tgggcaccgc cacaaattaa    3600
tcaaaggagt agaaagactc ttaggtggac aacaaggcac caatccttat ttgactttc    3660
actgtgttaa tcagggaacg attttgctgg atcttgctcc agaagataaa gaatatcagt    3720
cagtggaaga agagatgcaa agtactattc gagaacacag agatggtggt aatgctggcg    3780
gcatcttcaa cagatacaat gtcattcgaa ttcaaaaagt tgtcaacaag aagttgaggg    3840
agcggttctg ccaccgacag aaggaagtgt ctgaggagaa tcacaaccat cacaatgagc    3900
gcatgttgtt tcatggttct cctttcatta atgccattat tcataaaggg tttgatgagc    3960
gacatgcata cataggagga atgtttgggg ccgggattta ttttgctgaa aactcctcaa    4020
aaagcaacca atatgtttat ggaattggag gaggaacagg ctgccctaca cacaaggaca    4080
ggtcatgcta tatatgtcac agacaaatgc tcttctgtag agtgaccctt gggaaatcct    4140
ttctgcagtt tagcaccatg aaaatggccc acgcgcctcc agggcaccac tcagtcattg    4200
gtagaccgag cgtcaatggg ctggcatatg ctgaatatgt catctacaga ggagaacagg    4260
cataccccaga gtatcttatc acttaccaga tcatgaagcc agaagcccct tcccagaccg    4320
caacagccgc agagcagaag acctagtgaa tgcctgctgg tgaaggccag atcagatttc    4380
aacctgggac tggattacag aggattgttt ctaataacaa catcaatatt ctagaagtcc    4440
ctgacagcct agaaataagc tgtttgtctt ctataaagca ttgctatagt g             4491
```

<210> SEQ ID NO 5
<211> LENGTH: 6189
<212> TYPE: DNA
<213> ORGANISM: Homo Sapien

<400> SEQUENCE: 5

```
cgcgccgcct cgctagccga aacctgccca gccggtgccc ggccactgcg cacgcgcggg      60
acgacgtcac gtgcgctccc ggggctggac ggagctggca ggaggggcct tgccagcttc     120
cgccgccgcg tcgtttcagg acccggacgg cggattcgcg ctgcctccgc cgccgcgggg     180
cagccggggg gcagggagcc cagcgagggg cgcgcgtggg cgcggccatg ggactgcgcc     240
ggatccggtg acagcaggga gccaagcggc ccgggccctg agcgcgtctt ctccgggggg     300
cctcgccctc ctgctcgcgg ggccgggggct cctgctccgg ttgctggcgc tgttgctggc     360
tgtggcggcg gccaggatca tgtcgggtcg ccgctgcgcc ggcggggggag cggcctgcgc     420
gagcgccgcg gccgaggccg tggagccggc cgcccgagag ctgttcgagg cgtgccgcaa     480
cggggacgtg gaacgagtca gaggctggt gacgcctgag aaggtgaaca gccgcgacac     540
ggcgggcagg aaatccaccc cgctgcactt cgccgcaggt tttgggcgga agacgtagt     600
tgaatatttg cttcagaatg gtgcaaatgt ccaagcacgt gatgatgggg gccttattcc     660
tcttcataat gcatgctctt ttggtcatgc tgaagtagtc aatctccttt tgcgacatgg     720
tgcagacccc aatgctcgag ataattggaa ttatactcct ctccatgaag ctgcaattaa     780
aggaaagatt gatgtttgca ttgtgctgtt acagcatgga gctgagccaa ccatccgaaa     840
tacagatgga aggacagcat tggatttagc agatccatct gccaaagcag tgcttactgg     900
tgaatataag aaagatgaac tcttagaaag tgccaggagt ggcaatgaag aaaaaatgat     960
ggctctactc acaccattaa atgtcaactg ccacgcaagt gatggcagaa agtcaactcc    1020
attacatttg gcagcaggat ataacagagt aaagattgta cagctgttac tgcaacatgg    1080
agctgatgtc catgctaaag ataaaggtga tctggtacca ttacacaatg cctgttctta    1140
tggtcattat gaagtaactg aacttttggt caagcatggt gcctgtgtaa atgcaatgga    1200
cttgtggcaa ttcactcctc ttcatgaggc agcttctaag aacagggttg aagtatgttc    1260
tcttctctta agttatggtg cagacccaac actgctcaat tgtcacaata aaagtgctat    1320
agacttggct cccacaccac agttaaaaga aagattagca tatgaattta aggccactc     1380
gttgctgcaa gctgcacgag aagctgatgt tactcgaatc aaaaaacatc tctctctgga    1440
aatggtgaat tcaagcatc ctcaaacaca tgaaacagca ttgcattgtg ctgctgcatc     1500
tccatatccc aaaagaaagc aaatatgtga actgttgcta agaaaggag caaacatcaa    1560
tgaaaagact aaagaattct tgactcctct gcacgtggca tctgagaaag ctcataatga    1620
tgttgttgaa gtagtggtga acatgaagc aaaggttaat gctctggata atcttggtca    1680
gacttctcta cacagagctg catattgtgg tcatctacaa acctgccgcc tactcctgag    1740
ctatgggtgt gatcctaaca ttatatccct tcagggcttt actgctttac agatgggaaa    1800
tgaaaatgta cagcaactcc tccaagaggg tatctcatta ggtaattcag aggcagacag    1860
acaattgctg gaagctgcaa aggctggaga tgtcgaaact gtaaaaaaac tgtgtactgt    1920
tcagagtgtc aactgcagag acattgaagg gcgtcagtct acaccacttc attttgcagc    1980
tgggtataac agagtgtccg tggtggaata tctgctacag catggagctg atgtgcatgc    2040
taaagataaa ggaggccttg tacctttgca caatgcatgt tcttatggac attatgaagt    2100
tgcagaactt cttgttaaac atggagcagt agttaatgta gctgatttat ggaaatttac    2160
```

```
acctttacat gaagcagcag caaaaggaaa atatgaaatt tgcaaacttc tgctccagca    2220
tggtgcagac cctacaaaaa aaacaggga tggaaatact cctttggatc ttgttaaaga    2280
tggagataca gatattcaag atctgcttag gggagatgca gctttgctag atgctgccaa    2340
gaagggttgt ttagccagag tgaagaagtt gtcttctcct gataatgtaa attgccgcga    2400
tacccaaggc agacattcaa caccttttaca tttagcagct ggttataata atttagaagt    2460
tgcagagtat ttgttacaac acggagctga tgtgaatgcc caagacaaag gaggacttat    2520
tcctttacat aatgcagcat cttacgggca tgtagatgta gcagctctac taataaagta    2580
taatgcatgt gtcaatgcca cggacaaatg ggctttcaca cctttgcacg aagcagccca    2640
aaagggacga acacagcttt gtgctttgtt gctagcccat ggagctgacc cgactcttaa    2700
aaatcaggaa ggacaaacac ctttagattt agtttcagca gatgatgtca gcgctcttct    2760
gacagcagcc atgcccccat ctgctctgcc ctcttgttac aagcctcaag tgctcaatgg    2820
tgtgagaagc ccaggagcca ctgcagatgc tctctcttca ggtccatcta gcccatcaag    2880
cctttctgca gccagcagtc ttgacaactt atctgggagt ttttcagaac tgtcttcagt    2940
agttagttca agtggaacag agggtgcttc cagtttggag aaaaaggagg ttccaggagt    3000
agattttagc ataactcaat tcgtaaggaa tcttggactt gagcacctaa tggatatatt    3060
tgagagagaa cagatcactt tggatgtatt agttgagatg gggcacaagg agctgaagga    3120
gattggaatc aatgcttatg gacataggca caaactaatt aaaggagtcg agagacttat    3180
ctccggacaa caaggtctta acccatattt aactttgaac acctctggta gtggaacaat    3240
tcttatagat ctgtctcctg atgataaaga gtttcagtct gtggaggaag atgcaaag    3300
tacagttcga gagcacagag atggaggtca tgcaggtgga atcttcaaca gatcaaatat    3360
tctcaagatt cagaaggttt gtaacaagaa actatgggaa agatacactc accggagaaa    3420
agaagtttct gaagaaaacc acaaccatgc caatgaacga atgctatttc atgggtctcc    3480
ttttgtgaat gcaattatcc acaaaggctt tgatgaaagg catgcgtaca taggtggtat    3540
gtttggagct ggcattttatt ttgctgaaaa ctcttccaaa agcaatcaat atgtatatgg    3600
aattggagga ggtactgggt gtccagttca caaagacaga tcttgttaca tttgccacag    3660
gcagctgctc ttttgccggg taaccttggg aaagtctttc ctgcagttca gtgcaatgaa    3720
aatggcacat tctcctccag gtcatcactc agtcactggt aggcccagtg taaatggcct    3780
agcattagct gaatatgtta tttacagagg agaacaggct tatcctgagt atttaattac    3840
ttaccagatt atgaggcctg aaggtatggt cgatggataa atagttattt taagaaacta    3900
attccactga acctaaaatc atcaaagcag cagtggcctc tacgttttac tcctttgctg    3960
aaaaaaaatc atcttgccca caggcctgtg gcaaaaggat aaaaatgtga acgaagttta    4020
acattctgac ttgataaagc tttaataatg tacagtgttt tctaaatatt tcctgttttt    4080
tcagcacttt aacagatgcc attccaggtt aaactgggtt gtctgtacta aattataaac    4140
agagttaact tgaacctttt atatgttatg cattgattct aacaaactgt aatgccctca    4200
acagaactaa ttttactaat acaatactgt gttctttaaa acacagcatt tacactgaat    4260
acaatttcat ttgtaaaact gtaaataaga gcttttgtac tagcccagta tttatttaca    4320
ttgctttgta atataaatct gttttagaac tgcagcggtt tacaaaattt tttcatatgt    4380
attgttcatc tatacttcat cttacatcgt catgattgag tgatctttac atttgattcc    4440
agaggctatg ttcagttgtt agtttgggaaa gattgagtta tcagatttaa tttgccgatg    4500
ggagcctta tctgtcatta gaaatctttc tcatttaaga acttatgaat atgctgaaga    4560
```

```
tttaatttgt gataccttg tatgtatgag acacattcca aagagctcta actatgatag      4620
gtcctgatta ctaaagaagc ttctttactg gcctcaattt ctagctttca tgttggaaaa      4680
ttttctgcag tccttctgtg aaaattagag caaagtgctc ctgtttttta gagaaactaa      4740
atcttgctgt tgaacaatta ttgtgttctt ttcatggaac ataagtagga tgttaacatt      4800
tccagggtgg aagggtaat cctaaatcat ttcccaatct attctaatta ccttaaatct       4860 aaagggaaa aaaaaaatca caaacaggac tgggtagttt tttatcctaa gtatattttt       4920
tcctgttctt tttacttggt tttattgctg tatttatagc caatctatac atcatgggta      4980
aacttaaccc agaactataa aatgtagttg tttcagtccc cttcaggcct cctgaatggg      5040
caagtgcagt gaaacaggtg cttcctgctc ctgggttttc tctccatgat gttatgccca      5100
attggaaata tgctgtcagt ttgtgcacca tatggtgacc acgcctgtgc tcagtttggc      5160
agctatagaa ggaaatgctg tcccataaaa tgccatccct atttctaata taacactctt      5220
ttccaggaag catgcttaag catcttgtta cagagacata catccattat ggcttggcaa      5280
tctcttttat ttgttgactc tagctcccct caaagtcgag gaaagatctt tactcactta      5340
atgaggacat tccccatcac tgtctgtacc agttcacctt tattttacgt tttattcagt      5400
ctgtaaatta actggccctt tgcagtaact tgtacataaa gtgctagaaa atcatgttcc      5460
ttgtcctgag taagagttaa tcagagtaag tgcatttctg gagttgtttc tgtgatgtaa      5520
attatgatca ttatttaaga agtcaaatcc tgatcttgaa gtgcttttta tacagctctc      5580
taataattac aaatatccga aagtcatttc ttggaacaca agtggagtat gccaaatttt      5640
atatgaattt ttcagattat ctaagcttcc aggttttata attagaagat aatgagagaa      5700
ttaatggggt ttatatttac attatctctc aactatgtag cccatattac tcaccctatg      5760
agtgaatctg gaattgcttt tcatgtgaaa tcattgtggt ctatgagttt acaatactgc      5820
aaactgtgtt attttatcta aaccattgct taatgagtgt gttttccat gaatgaatat       5880 accgtggttc atatgttagc atggcagcat tttcagatag cttttgtttt gttgggaagt      5940
tggggttttg gggggagggg gagtattagt acgttgcatg gaatagccta ctttataatg      6000
atgggaatgc tttttctttt gttttgggat tttttttttt gaagtgaaat ttaactttt       6060 gtgccagtag tactattata cccatcttca gtgtcttact tgtactgtat caaattccat      6120
accctcattt aattcttaat aaaactgttc acttgtaaaa aaaaaaaaa aaaaaaaaa        6180 aaaaaaaaa                                                              6189

<210> SEQ ID NO 6
<211> LENGTH: 5490
<212> TYPE: DNA
<213> ORGANISM: Homo Sapien

<400> SEQUENCE: 6
cgcccgccca gccccggggg cagggaaagc ctaaattacg gaattaccgc gagcaaggag        60
cgcggaatcg gggagcgtcc ggagctagct ggatcctcta ggcaggatgg tgatgggaat      120
ctttgcaaat tgtatcttct gtttgaaagt gaagtactta cctcagcagc agaagaaaaa      180
gctacaaact gacattaagg aaaatggcgg aaagttttcc ttttcgttaa atcctcagtg      240
cacacatata atcttagata atgctgatgt tctgagtcag taccaactga attctatcca      300
aaagaaccac gttcatattg caaacccaga ttttatatgg aaatctatca gagaaaagag      360
actcttggat gtaaagaatt atgatcctta taagcccctg acatcacac cacctcctga       420
```

| | |
|---|---|
| tcagaaggcg agcagttctg aagtgaaaac agaaggtcta tgcccggaca gtgccacaga | 480 |
| ggaggaagac actgtggaac tcactgagtt tggtatgcag aatgttgaaa ttcctcatct | 540 |
| tcctcaagat tttgaagttg caaaatataa caccttggag aaagtgggaa tggagggagg | 600 |
| ccaggaagct gtggtggtgg agcttcagtg ttcgcgggac tccagggact gtcctttcct | 660 |
| gatatcctca cacttcctcc tggatgatgg catggagact agaagacagt ttgctataaa | 720 |
| gaaaacctct gaagatgcaa gtgaatactt tgaaaattac attgaagaac tgaagaaaca | 780 |
| aggatttcta ctaagagaac atttcacacc tgaagcaacc caattagcat ctgaacaatt | 840 |
| gcaagcattg cttttggagg aagtcatgaa ttcaagcact ctgagccaag aggtgagcga | 900 |
| tttagtagag atgatttggg cagaggccct gggccacctg aacacatgc ttctcaagcc | 960 |
| agtgaacagg attagcctca cgatgtgag caaggcagag gggattctcc ttctagtaaa | 1020 |
| ggcagcactg aaaaatggag aaacagcaga gcaattgcaa aagatgatga cagagtttta | 1080 |
| cagactgata cctcacaaag gcacaatgcc caaagaagtg aacctgggac tattggctaa | 1140 |
| gaaagcagac ctctgccagc taataagaga catggttaat gtctgtgaaa ctaatttgtc | 1200 |
| caaacccaac ccaccatccc tggccaaata ccgagctttg aggtgcaaaa ttgagcatgt | 1260 |
| tgaacagaat actgaagaat tctcagggt tagaaaagag gttttgcaga atcatcacag | 1320 |
| taagagccca gtgatgtct tgcagatatt tagagttggc agagtgaatg aaaccacaga | 1380 |
| gtttttgagc aaacttggta atgtgaggcc cttgttgcat ggttctcctg tacaaaacat | 1440 |
| cgtgggaatc ttgtgtcgag ggttgctttt acccaaagta gtggaagatc gtggtgtgca | 1500 |
| aagaacagac gtcggaaacc ttggaagtgg gatttatttc agtgattcgc tcagtacaag | 1560 |
| tatcaagtac tcacacccgg gagagacaga tggcaccaga ctcctgctca tttgtgacgt | 1620 |
| agccctcgga aagtgtatgg acttacatga gaaggacttt cccttaactg aagcaccacc | 1680 |
| aggctacgac agtgtgcatg gagtttcaca aacagcctct gtcaccacag actttgagga | 1740 |
| tgatgaattt gttgtctata aaaccaatca ggttaaaatg aaatatatta ttaaattttc | 1800 |
| catgcctgga gatcagataa aggactttca tcctagtgat catactgaat tagaggaata | 1860 |
| cagacctgag tttcaaatt tttcaaaggt tgaagattac cagttaccag atgccaaaac | 1920 |
| ttccagcagc accaaggccg gcctccagga tgcctctggg aacttggttc tctggagga | 1980 |
| tgtccacatc aaagggagaa tcatagacac tgtagcccag gtcattgttt ttcagacata | 2040 |
| cacaaataaa agtcacgtgc ccattgaggc aaaatatatc tttcctttgg atgacaaggc | 2100 |
| cgctgtgtgt ggcttcgaag cctttcatca atgggaagcac atagttggag agattaaaga | 2160 |
| gaaggaagaa gcccagcaag agtacctaga agccgtgacc cagggccatg cgcttacct | 2220 |
| gatgagtcag gatgctccgg acgtttttac tgtaagtgtt ggaaacttac cccctaaggc | 2280 |
| taaggttctt ataaaaatta cctacatcac agaactcagc atcctgggca ctgttggtgt | 2340 |
| cttttttcatg cccgccaccg tagcaccctg gcaacaggaa aaggctttga atgaaaacct | 2400 |
| tcaggataca gtagagaaga tttgtataaa agaaatagga acaaagcaaa gcttctcttt | 2460 |
| gactatgtct attgagatgc cgtatgtgat tgaattcatt ttcagtgata cacatgaact | 2520 |
| gaaacaaaag cgcacagact gcaaagctgt cattagcacc atggaaggca gctccttaga | 2580 |
| cagcagtgga ttttctctcc acatcggttt gtctgctgcc tatctcccaa gaatgtgggt | 2640 |
| tgaaaaacat ccagaaaaag aaagcgaggc ttgcatgctt gtctttcaac ccgatctcga | 2700 |
| tgtcgacctc cctgacctag ccagtgagag cgaagtgatt atttgtcttg actgctccag | 2760 |
| ttccatggag ggtgtgacat tcttgcaagc caagcaaatc accttgcatg cgctgtcctt | 2820 |

```
ggtgggtgag aagcagaaag taaatattat ccagttcggc acaggttaca aggagctatt    2880
ttcgtatcct aagcatatca caagcaatac cacggcagca gagttcatca tgtctgccac    2940
acctaccatg gggaacacag acttctggaa aacactccga tatcttagct tattgtaccc    3000
tgctcgaggg tcacggaaca tcctcctggt gtctgatggg cacctccagg atgagagcct    3060
gacattacag ctcgtgaaga ggagccgccc gcacaccagg ttattcgcct gcggtatcgg    3120
ttctacagca atcgtcacg tcttaaggat tttgtcccag tgtggtgccg gagtatttga     3180
atattttaat gcaaaatcca agcatagttg gagaaaacag atagaagacc aaatgaccag    3240
gctatgttct ccgagttgcc actctgtctc cgtcaaatgg cagcaactca atccagatgc    3300
gcccgaggcc ctgcaggccc cagcccaggt gccatccttg tttcgcaatg atcgactcct    3360
tgtctatgga ttcattcctc actgcacaca agcaactctg tgtgcactaa ttcaagagaa    3420
agaattttgt acaatggtgt cgactactga gcttcagaag acaactggaa ctatgatcca    3480
caagctggca gcccgagctc taatcagaga ttatgaagat ggcattcttc acgaaaatga    3540
aaccagtcat gagatgaaaa acaaaacctt gaaatctctg attattaaac tcagtaaaga    3600
aaactctctc ataacacaat ttacaagctt tgtggcagtt gagaaaaggg atgagaatga    3660
gtcgcctttt cctgatattc caaaagtttc tgaacttatt gccaagaag atgtagactt      3720 cctgccctac atgagctggc aggggagcc ccaagaagcc gtcaggaacc agtctctttt     3780
agcatcctct gagtggccag aattacgttt atccaaacga aaacatagga aaattccatt    3840
ttccaaaaga aaaatggaat tatctcagcc agaagtttct gaagattttg aagaggatgg    3900
cttaggtgta ctaccagctt tcacatcaaa tttggaacgt ggaggtgtgg aaaagctatt    3960
ggatttaagt tggacagagt catgtaaacc aacagcaact gaaccactat ttaagaaagt    4020
cagtccatgg gaaacatcta cttctagctt ttttcctatt ttggctccgg ccgttggttc    4080
ctatcttacc ccgactaccc gcgctcacag tcctgcttcc ttgtctttg cctcatatcg      4140 tcaggtagct agtttcggtt cagctgctcc tcccagacag tttgatgcat ctcaattcag    4200
ccaaggccct gtgcctggca cttgtgctga ctggatccca cagtcggcgt cttgtcccac    4260
aggacctccc cagaacccac cttctgcacc ctattgtggc attgtttttt cagggagctc    4320
attaagctct gcacagtctg ctccactgca acatcctgga ggctttacta ccaggccttc    4380
tgctggcacc ttccctgagc tggattctcc ccagcttcat ttctctcttc ctacagaccc    4440
tgatcccatc agaggttttg ggtcttatca tccctctgct tactctcctt ttcattttca    4500
accttccgca gcctctttga ctgccaacct taggctgcca atggcctctg ctttacctga    4560
ggctctttgc agtcagtccc ggactacccc agtagatctc tgtcttctag aagaatcagt    4620
aggcagtctc gaaggaagtc gatgtcctgt ctttgctttt caaagttctg acacagaaag    4680
tgatgagcta tcagaagtac ttcaagacag ctgcttttta caaataaagt gtgatacaaa    4740
agatgacagt atcccgtgct ttctggaatt aaaagaagag gatgaaatag tgtgcacaca    4800
acactggcag gatgctgtgc cttggacaga actcctcagt ctacagacag aggatggctt    4860
ctggaaactt acaccagaac tgggacttat attaaatctt aatacaaatg gtttgcacag    4920
ctttcttaaa caaaaaggca ttcaatctct aggtgtaaaa ggaagagaat gtctcctgga    4980
cctaattgcc acaatgctgg tactacagtt tattcgcacc aggttggaaa agagggaat     5040 agtgttcaaa tcactgatga aaatggatga cccttctatt tccaggaata ttccctgggc    5100
ttttgaggca ataaagcaag caagtgaatg ggtaagaaga actgaaggac agtacccatc    5160
```

-continued

| | | | | |
|---|---|---|---|---|
| tatctgccca | cggcttgaac | tggggaacga | ctgggactct | gccaccaagc agttgctggg | 5220 |
| actccagccc | ataagcactg | tgtcccctct | tcatagagtc | ctccattaca gtcaaggcta | 5280 |
| agtcaaatga | aactgaattt | taaacttttt | gcatgcttct | atgtagaaaa taatcaaatg | 5340 |
| ataatagata | attataatga | aacttcatta | aggtttcatt | cagtgtagca attactgtct | 5400 |
| ttaaaaatta | agtggaagaa | gaattacttt | aatcaactaa | caagcaataa taaaatgaaa | 5460 |
| cttaaaataa | aaaaaaaaaa | aaaaaaaaaa | | | 5490 |

THERAPEUTIC COMPOUNDS

This invention relates to a series of compounds derived which are derivatives of tricyclic lactam indoles and tricyclic lactam benzimidazoles and which inhibit poly (ADP-ribose) polymerase (PARP) and their use in the treatment of cancer, in particular breast cancer.

Homologous recombination (HR) has been shown to play an important role in repair of damage occurring at DNA replication forks in mammalian cells (2). Thus, cells deficient in HR show retarded growth and exhibit higher levels of genetic instability. It is believed that genetic instability due to loss of HR repair in human cancers significantly contributes to the development of cancer in these cells (1).

Post transcriptional modification of nuclear proteins by poly (ADP-ribosyl)ation in response to DNA strand breaks plays an important role in DNA repair, regulation of apoptosis, and maintenance of genomic stability.

Poly (ADP-ribose) polymerase (PARP-1) (SEQ ID NO: 1 in the accompanying "Sequence Listing") is the principal member of the PARP enzyme family and is an abundant nuclear protein in mammalian cells. PARP-1 catalyses the formation of poly (ADP-ribose) (PAR) polymers using NAD$^+$ as substrate. Upon DNA damage, PARP-1 binds rapidly to a DNA single-strand break (SSB) and catalyses the addition of negatively charged PAR chains to itself (automodification) and other proteins [see(3,4) for reviews]. The binding of PARP-1 to SSBs is believed to protect DNA lesions from further processing until PARP-1 is dissociated from the break by the accumulated negative charge resulting from PAP polymers (5,6).

Other members of the PARP family include PARP-2 (SEQ ID NO: 2 in the accompanying "Sequence Listing"), PARP-3 (SEQ ID NO: 3 in the accompanying "Sequence Listing"), Tankyrase-1 (SEQ ID NO:4 in the accompanying "Sequence Listing"), Tankyrase-2 (SEQ ID NO:5 in the accompanying "Sequence Listing"), and VPARP (SEQ ID NO:6 in the accompanying "Sequence Listing"). These members are homologous with PARP-1 and can make ADP-ribose polymers from NAD by the same catalytic mechanism as PARP-1.

Although PARP-1 has been implicated in several nuclear processes, such as modulation of chromatin structure, DNA-replication, DNA repair and transcription, PARP-1 knockout mice develop normally (7). Cells isolated from these mice exhibit a hyper recombination phenotype and genetic instability in the form of increased levels of sister chromatic exchanges (SCE) micronuclei and tetraploidy (8, 10). Genetic instability may also occur in these PARP-1 knockout mice through telomere shortening, increased frequency of chromosome fusion and aneuploid (11), although all these results could not be repeated in another set of PARP-1 knockout mice (12). In the former mice knockout, PARP-1 null mutation rescued impaired V (D) J recombination in SCID mice (13).

These results support the view suggested by Lindahl and co-workers that PARP-1 has a protective role against recombination (5). It was proposed that binding of PARP-1 to ssDNA breaks prevents the recombination machinery from recognising and processing DNA lesions or, alternatively that the negative charges accumulated following poly (ADP-ribosyl)ation repel adjacent recombinogenic DNA sequences. Only the latter model is consistent with inhibition of PARP-1 itself and expression of a dominant negative mutant PARP-1, including SCE, gene amplification and homologous recombination (14-18).

Studies based on treating cells with inhibitors of PARP-1 or cells derived from PARP-1 knockout mice indicate that the suppression of PARP-1 activity increases cell susceptibility to DNA damaging agents and inhibits strand break rejoining (3, 4, 8-11, 19, 20).

Inhibitors of PARP-1 activity have been used in combination with traditional cancer treatment regimes such as radio-therapy and chemotherapy (21). When the inhibitors were used in combination with methylating agents, topoisomerase poisons and ionising radiations they were found to enhance the effectiveness of these forms of treatment. However, such treatments are non-selective and as such cause damage and death to non-cancerous or 'healthy' cells. Furthermore, such treatments are known to give rise to unpleasant side effects.

Therefore, it is highly desirable to provide a treatment for cancer that is both effective and selective in the killing of cancer cells and which does not need to be administered in combination with radio-therapy or chemotherapy treatments.

Surprisingly it has been found that cells deficient in homologous recombination (HR) are hypersensitive to PARP inhibitors relative to wild type cells.

Thus, according to a first aspect of the present invention there is provided a compound for inhibiting the activity of PARP having formula I:

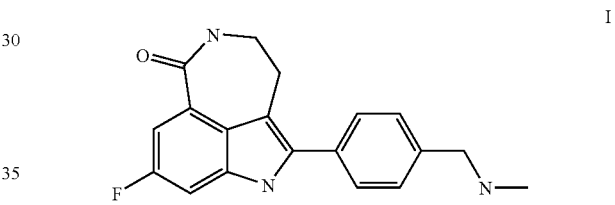

and pharmaceutically acceptable salts thereof.

According to a second aspect of the present invention there is provided a compound for inhibiting the activity of PARP having formula II:

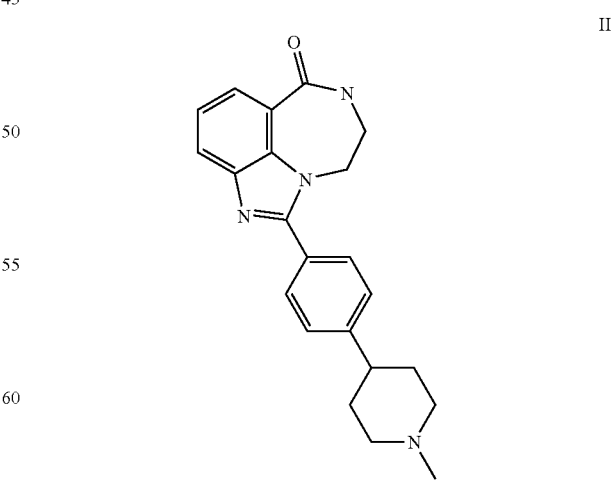

and pharmaceutically acceptable salts thereof.

According to a third aspect of the present invention there is provided a compound for inhibiting the activity of PARP having formula III:

III

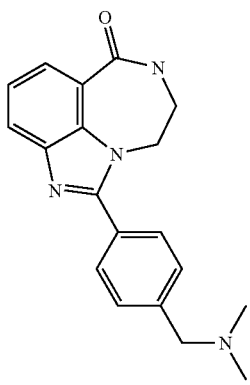

and pharmaceutically acceptable salts thereof.

The compounds described herein can be prepared by synthetic routes based on those disclosed in WO 00/42040 and WO 01/16136.

It will be understood that where reference is made in this specification to compounds of formulas I to III the reference should be construed as extending also to their pharmaceutically acceptable salts and to other pharmaceutically acceptable bioprecursors (prodrug forms) where relevant. The term "prodrug" is used in the present specification to denote modified forms or derivatives of a pharmacologically active compound which biodegrade or are modified in vivo so as to become converted into said active compound after administration, especially oral or intravenous administration, in the course of therapeutic treatment of a mammal. Such prodrugs are commonly chosen because of an enhanced solubility in aqueous media which helps to overcome formulation problems, and also in some cases to give a relatively slow or controlled release of the active agent.

As referred to herein pharmaceutically acceptable salts include metal salts, phosphates and quaternary amines. The metal salts may be formed with alkali metals such as lithium, sodium or potassium.

Preferably, formula I, above, is administered in the form of a pharmaceutically acceptable phosphate salt having the follwing formula:

Formula I-phosphate

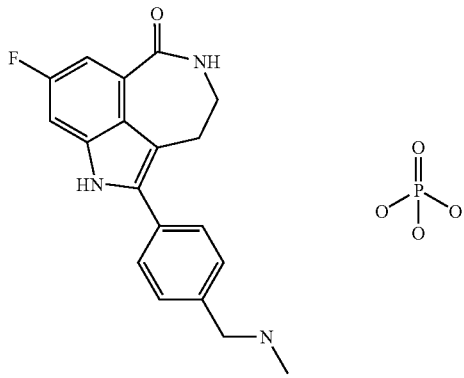

The present invention also relates to the therapeutic utility of the compounds described herein.

Thus, according to a further aspect of the present invention there is provided the use of a therapeutic amount of a compound of formula I, and pharmaceutically acceptable salts thereof, in the manufacture of a medicament.

According to a further aspect of the present invention there is provided the use of a therapeutic amount of a compound of formula II, and pharmaceutically acceptable salts thereof, in the manufacture of a medicament.

According to a further aspect of the present invention there is provided the use of a therapeutic amount of a compound of formula III, and pharmaceutically acceptable salts thereof, in the manufacture of a medicament.

According to a further aspect of the present invention there is provided the use of a therapeutic amount of a compound of formula I, and pharmaceutically acceptable salts thereof, in the manufacture of a medicament for the treatment of a disease or condition that is caused by a genetic defect in a gene that mediates homologous recombination.

According to a further aspect of the present invention there is provided the use of a compound of formula II in the manufacture of a medicament for the treatment of a disease or condition that is caused by a genetic defect in a gene that mediates homologous recombination.

According to a further aspect of the present invention there is provided the use of a compound of formula III in the manufacture of a medicament for the treatment of a disease or condition that is caused by a genetic defect in a gene that mediates homologous recombination.

Diseases and conditions which are caused by a genetic defect in a gene that mediates homologous recombination include, but are not limited to cancer, in particular breast cancer.

As referred herein "cancer" or "tumour" includes, but is not limited to, cancer of the lung, colon, pancreas, stomach, ovary, cervix, breast, prostate bone, brain or skin.

The use of PARP inhibitors is particularly suitable in the treatment of cancer which is caused by a genetic defect in a gene wherein the said gene mediates homologous recombinations. Cancer cells of this type tend to be HR defective.

The specific sensitivity of HR defective tumours to PARP inhibition means that normally dividing "healthy" cells in patients which have adequate amounts of HR will be largely unaffected by the treatment.

A further advantage of treatment using PARP inhibitors is that the PARP inhibitors do not need to be administered as a combination therapy along with conventional radiotherapy or chemotherapy treatments thereby avoiding the side effects associated with these conventional forms of treatment.

A defect in a gene that mediates homologous recombination may be due to a mutation in, the absence of, or defective expression of, a gene encoding a protein involved in HR.

According to a further aspect of the present invention there is provided the use of a therapeutic amount of a compound of formula I in the manufacture of a medicament for inducing apoptosis in HR defective cells.

According to a further aspect of the present invention there is provided the use of a therapeutic amount of a compound of formula II in the manufacture of a medicament for inducing apoptosis in HR defective cells.

According to a further aspect of the present invention there is provided the use of a therapeutic amount of a compound of formula III in the manufacture of a medicament for inducing apoptosis in HR defective cells.

According to a further aspect of the present invention there is provided the use of a therapeutic amount of a compound of formula I in the manufacture of a medicament for the treatment of cancer.

According to a further aspect of the present invention there is provided the use of a therapeutic amount of a compound of formula II in the manufacture of a medicament for the treatment of cancer.

According to a further aspect of the present invention there is provided the use of a therapeutic amount of a compound of formula III in the manufacture of a medicament for the treatment of cancer.

Cancer cells suitable for treatment with the compounds described herein may be partially or totally deficient in HR. Preferably, the cells are totally deficient in HR.

The compounds described herein may be used to treat an inherited form of cancer wherein the patient to be treated has a familial predisposition to the cancer. However the said compounds are particularly suitable for the treatment of gene-linked hereditary cancer, and most particularly gene-linked hereditary breast cancer.

In a preferred aspect, the PARP inhibitor is useful in the treatment of cancer cells defective in the expression of a gene involved in HR. Genes with suggested function in HR include XRCC1, ADPRT (PARP-1), ADPRTL2, (PARP02) CTPS, RPA, RPA1, RPA2, RPA3, XPD, ERCC1, XPF, MMS19, RAD51, RAD51β, RAD51C, RAD51D, DMC1, XRCCR, XRCC3, BRCA1, BRCA2, RAD52, RAD54, RAD50, MRE11, NB51, WRN, BLM KU70, RU80, ATM, ATR CHK1, CHK2, FANCA, FANCB, FANCC, FANCD1, FANCD2, FANCE, FANCF, FANCG, FANCC, FANCD1, FANCD2, FANCE, FANCF, FANCG, RAD1, RAD9 [See (2, 3, 5, 22-28) for reviews].

A gene involved in HR may be a tumour suppressor gene. The invention thus provides for the treatment of cancer cells defective in the expression of a tumour suppressor gene. Preferably, the tumour suppressor gene is BRCA1 or BRCA2.

Breast cancer is the most common type of cancer among women in the Western World. Certain families have a strong predisposition for breast cancer, which is often owing to an inherited mutation in one allele of either BRCA1 or BRCA2. However, one functional allele is maintained. Thus, individuals possessing the said mutation develop normally and have no phenotypic consequence from this mutation. However, in one cell, the functional allele might be lost, making this cell cancerous and at the same time deficient in HR. This step is critical for the onset of a tumour (1).

Therefore, according to a still further aspect of the invention there is provided the use of a therapeutic amount of a compound of formula I in the manufacture of a medicament for the treatment of cancer cells defective in BRCA1 and/or BRCA2 expression.

According to a further aspect of the present invention there is provided the use of a therapeutic amount of a compound of formula II in the manufacture of a medicament for the treatment of cancer cells defective in BRCA1 and/or BRCA2 expression.

According to a further aspect of the present invention there is provided the use of a therapeutic amount of a compound of formula III in the manufacture of a medicament for the treatment of cancer cells defective in BRCA1 and/or BRCA2 expression.

The cancer cells to be treated may be partially or totally deficient in BRCA1 or BRCA2 expression. Such deficiencies can be identified using multiplex PCR techniques array techniques (29, 30) or using other screens known to the skilled person. Particularly useful techniques include real-time quantitative RT-PCR, Northern blot, immunohistochemistry and Western Blot (31, 32).

Accordingly, the compounds of the present invention are of particular interest for the treatment of a range of selected cancer tumours, and the invention further provides a method for the treatment of a patient suffering from cancer.

The compounds described herein may be administered in a therapeutically effective non-toxic amount via any suitable route for effectively targeting cancer cells. Suitable administration routes include, but are not limited to, any of the following: oral, intravenous, intramuscular, intradermal, intranasal, or topical.

A therapeutically effective amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease.

For administration to mammals, and particularly humans, it is expected that the daily dosage level of the active agent will be from 0.01 to 50 mg/kg in mice and 0.01 mg/m$^2$ to 50 mg/m$^2$ body surface area in humans. Ultimately, however, the amount of active ingredient administered and the frequency of administration will be at the discretion of a physician.

Advantageously, only very low doses of PARP inhibiting compounds are needed to have a therapeutic effect in treating cancer thereby reducing systemic build up of the compounds and thus minimising any associated toxic effects.

While it may be possible for the compounds described herein to be administered alone as the 'raw' compound, it is preferable to present the compounds in a pharmaceutical composition.

All methods of formulation in making up such pharmaceutical compositions will generally include the step of bringing one of the compounds described herein into association with a carrier which constitutes one or more accessory ingredients. Usually, the formulations are prepared by uniformly and intimately bringing the compound of formula I into association with a liquid carrier or with a finely divided solid carrier or with both and then, if necessary, shaping the product into desired formulations.

Formulations of the present invention suitable for oral administration may be presented as discrete units such as capsules, cachets, tablets or lozenges, each containing a predetermined amount of one of the compounds describe herein; as a powder or granules; or a suspension in an aqueous liquid or non-aqueous liquid such as a syrup, an elixir, an emulsion or a draught. Any one of the compounds described herein may also be presented as a bolus, electuary or paste.

A tablet may be made by compression or moulding, optionally with one or more accessory ingredients. Compressed tables may be prepared by compressing, in a suitable machine, any one of the compounds described herein in a free-flowing form such as a powder or granules, optionally mixed with a binder, lubricant, inert diluent, surface active or dispersing agent. Moulded tables may be made by moulding, in a suitable machine, a mixture of any one of the powdered compound described herein with any suitable carrier.

A syrup may be made by adding any one of the compounds described herein to a concentrated, aqueous solution of a sugar, for example sucrose, to which may be added any desired accessory ingredient. Such accessory ingredient(s) may include flavourings, an agent to retard crystallisation of the sugar or an agent to increase the solubility of any other ingredient, such as a polyhydric alcohol, for example glycerol or sorbitol.

Formulations for rectal administration may be presented as a suppository with a usual carrier such as cocoa butter.

Formulations suitable for parenteral administration conveniently comprise a sterile aqueous preparation of any one of the compounds describe herein which is preferably isotonic with the blood for the recipient.

In addition to the aforementioned ingredients, formulations of this invention, for example ointments, creams and the like, may include one or more accessory ingredients, for example a diluent, buffer, flavouring agent, binder, surface active agent, thickener, lubricant and/or a preservative (including an antioxidant) or other pharmaceutically inert excipient.

The compounds of this invention may also be made up for administration in liposomal formulations which can be prepared by methods well-known in the art.

Thus, according to a further aspect of the present invention there is provided a pharmaceutical composition comprising a compound of formula I, or pharmaceutically acceptable salt thereof, as an active agent.

According to a further aspect of the present invention there is provided a pharmaceutical composition comprising a compound of formula II, or pharmaceutically acceptable salt thereof, as an active agent.

According to a further aspect of the present invention there is provided a pharmaceutical composition comprising a compound of formula III, or pharmaceutically acceptable salt thereof, as an active agent.

The pharmaceutical composition may further comprise at least one other ingredient providing a compatible pharmaceutically acceptable additive, carrier diluent carrier or excipient and may be presented in unit dosage form.

The carrier(s) must be pharmaceutically acceptable in the sense of being compatible with the other ingredients of the formulation and not deterious to the recipient thereof.

The possible formulations include those suitable for oral, rectal, topical and parenteral (including subcutaneous, intramuscular and intravenous) administration or for administration to the lung or another absorptive site such as the nasal passages.

The compounds referred to herein may be administered in combination with other anti-cancer compounds.

The present invention also includes a method of treating cancer in mammals by administering the compounds described herein and their pharmaceutically acceptable salts.

Thus, according to a further aspect of the present invention there is provided a method for the treatment of cancer in mammals comprising administering a compound of formula I, or a pharmaceutically acceptable salt thereof.

Thus, according to a further aspect of the present invention there is provided a method for the treatment of cancer in mammals comprising administering a compound of formula II, or a pharmaceutically acceptable salt thereof:

Thus, according to a further aspect of the present invention there is provided a method for the treatment of cancer in mammals comprising administering a compound of formula III, or a pharmaceutically acceptable salt thereof:

The present invention will now be described by way of example only with reference to the accompanying figures wherein:

FIG. 1 shows the percentage survival of AA8, IrS ISF and CxR3 cell lines when treated with various concentrations of the compound of formula III. Formula III was found to be most active against IrS ISF, which lacks XRCC3, having an $LC_{50}$ (the concentration of the active component that kills 50% of the cells) of 100 nM.

FIG. 2 shows the percentage survival of V79-Z, VC8 and VC8B2 cell lines when treated with various concentrations of the compound of formula III. Formula III was found to be most effective against the VC8 cell line, which lacks BRCA2, having an $LC_{50}$ value of 43 nM and an $LC_{90}$ (concentration of active component that kills 90% of the cells) was 1200 nM.

Figure 3:
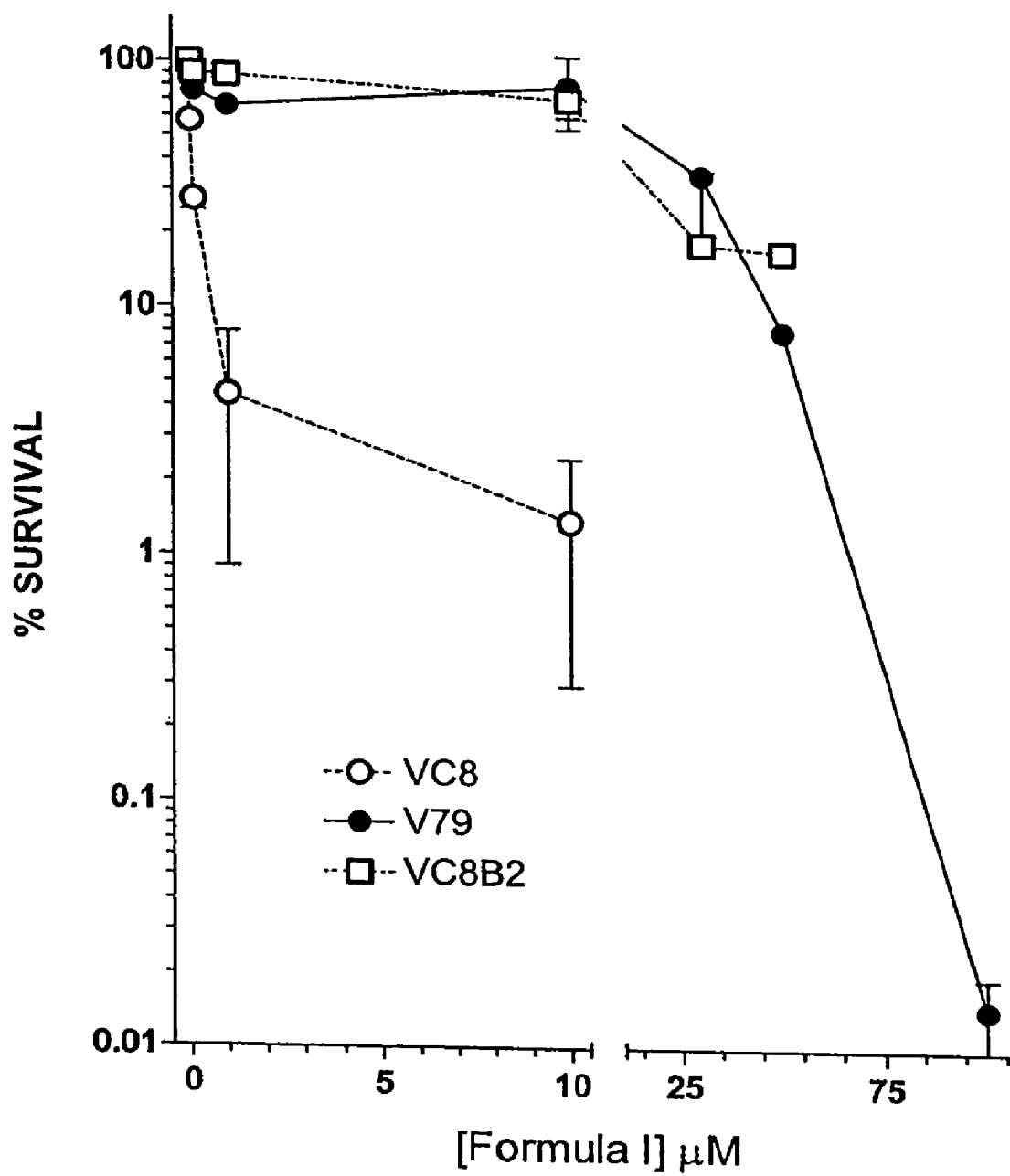
FIG. 3 is a graph showing cell survival in the presence of PARP inhibitor of formula I in V79 cell line, VC8 cell line and VC8B2 cell line.
Figure 4:
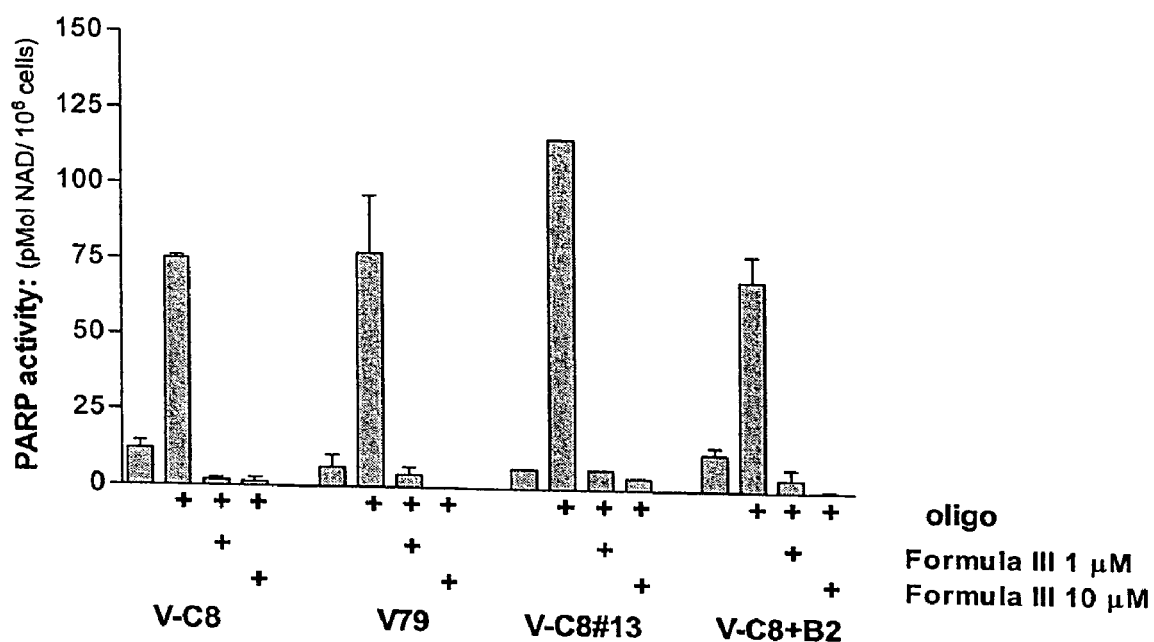
FIG. 4 is a bar chart showing PARP activity in VC8, V79, VC8#13 and VC8, VC8#13 and VC8+B2 cell lines in the presence of PARP inhibitor of formula III.

FIG. 3 shows the percentage survival of V79-Z, VC8 and VC8B2 cell lines when treated with various concentrations of the compound of formula I. Formula I was found to be most effective against the VC8 cell line, which lacks BRCA2, having an $LC_{50}$ value of 12 nM, $LC_{90}$ was 27 nM FIG. 4 shows PARP activity of various cell lines when treated with various concentrations of the compound of formula III. The graph of FIG. 3 is divided into four result sets for each respective cell line. The first bar of each set shows the background PARP activity (no oligo present, so PARP activity is dependent upon endogenous DNA breaks), the second bar is total stimulatable (by oligo) PARP activity and the third and fourth bars show the PARP activity in the presence of the compound of formula III.

Figure 5:
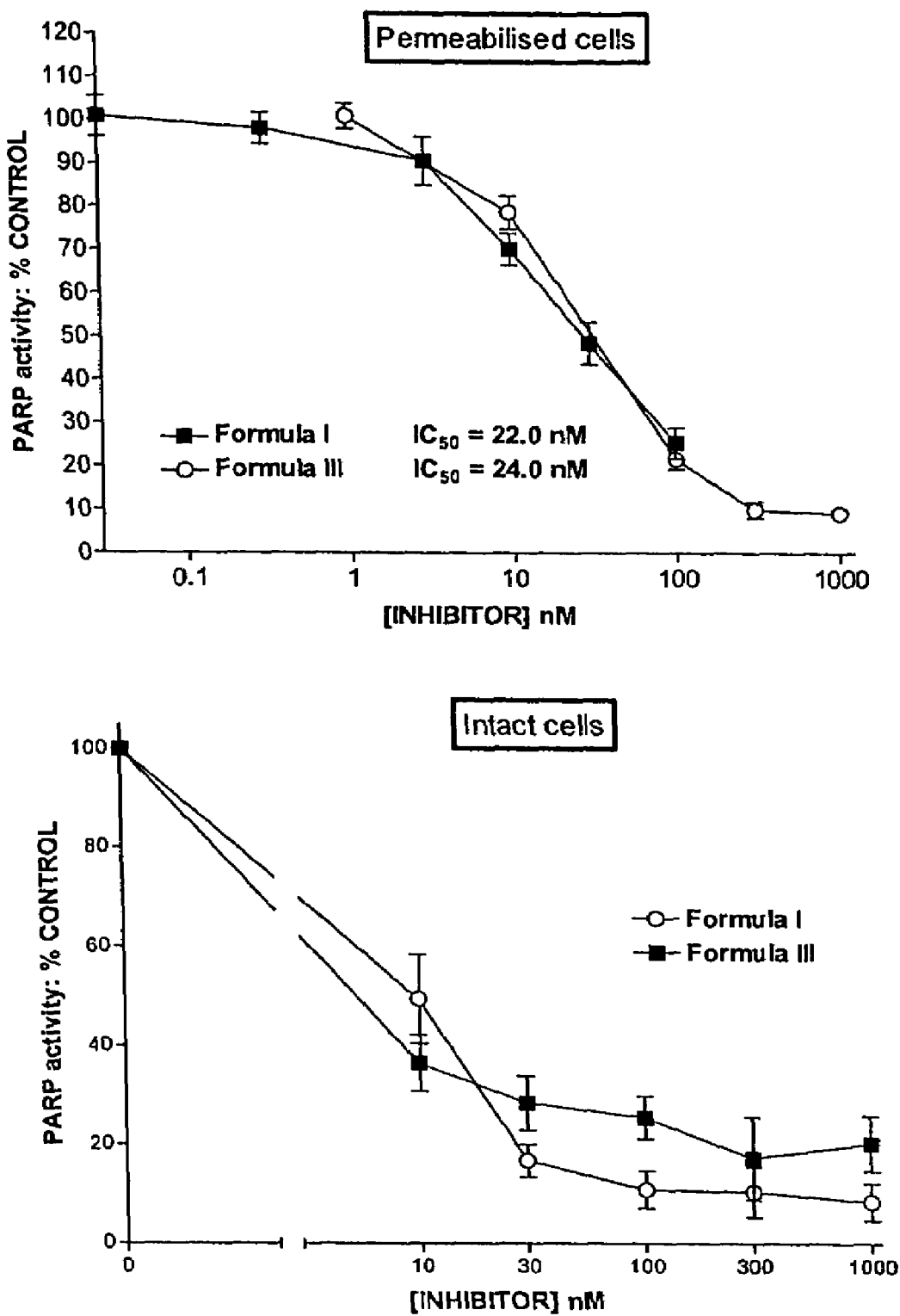
FIG. 5 is a pair of graphs showing inhibition of cellular PARP activity in the presence of PARP inhibitor of formula I and III in permeabilised (upper graph) and intact (lower graph) L1210 cells.

FIG. 5 shows the effect of Compounds Formula I and III on PARP activity.

Cells used to obtain the results shown in FIG. 5 were either permeabilised with digitonin and then assayed for total stimulatable (by oligo) PARP activity in the presence and absence of PARP inhibitor of formula I and formula III or exposed to one of said PARP inhibitors for 20 minutes prior to permeabilisation and assayed for total stimulatable PARP activity.

There was no difference in the PARP inhibitory activity of the compounds of formula I and formula III when the cells were permeabilised prior to adding the inhibitor compound but the compound of formula I was more potent in intact cells, possibly because it accumulates within cells to a higher degree.

Figure 6:
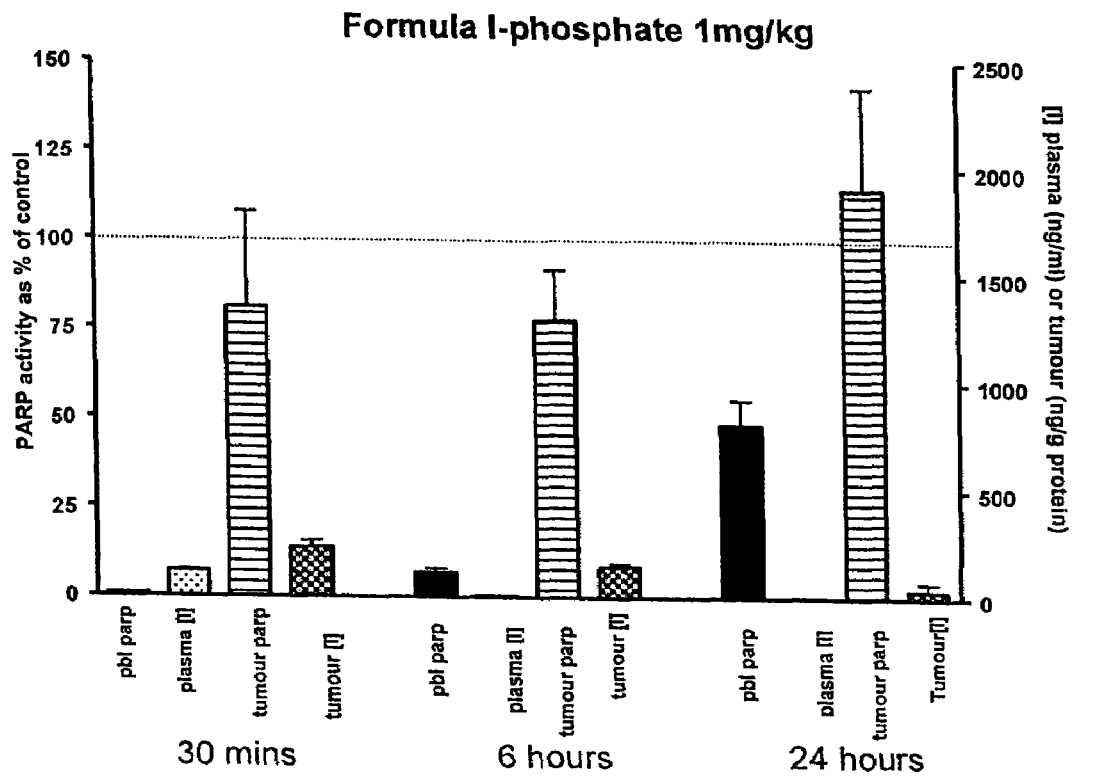
FIG. 6 is a pair of bar charts showing the blood and tumour pharmacokinetics and pharmacodynamics with formula I-phosphate at 1 mg/kg (upper) and 10 mg/kg (lower) in mice bearing SW620 xenografts.
Figure 6:
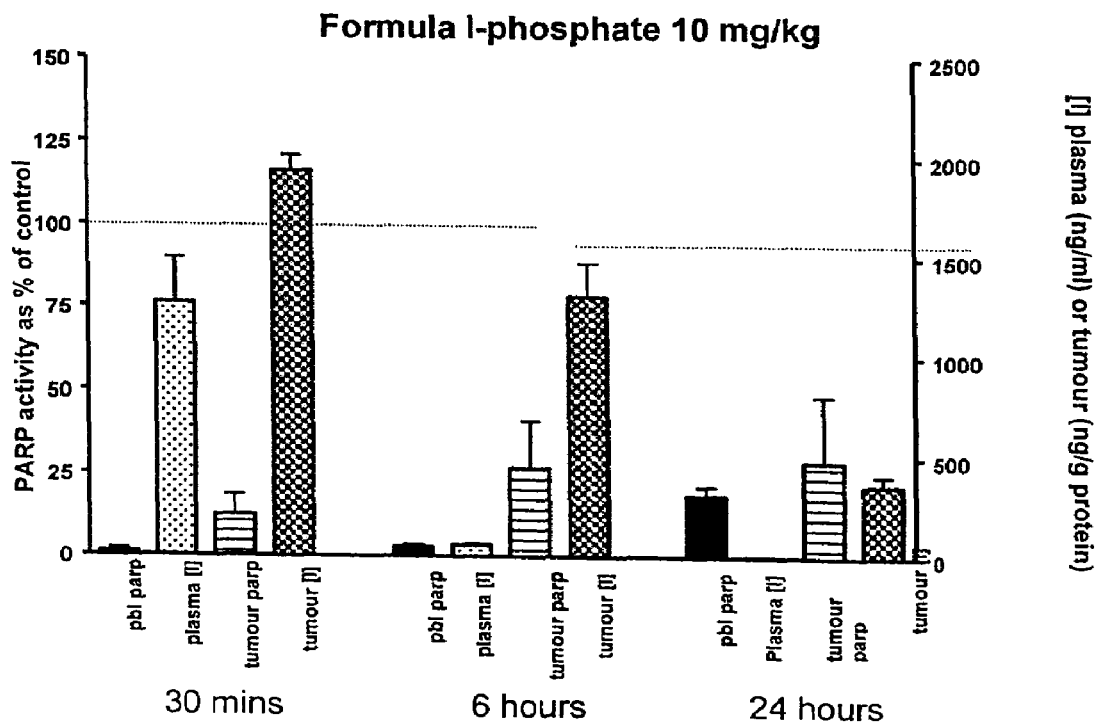

FIG. 6 shows the plasma and tumour concentrations of the compound of formula I, and its pharmacokinetic effect on mouse peripheral blood lymphocytes (pbl parp) and SW620 xenografts (tumour PARP), at various times following intraperitoneal administration of the phosphate salt of compound of formula I. The phosphate salt of the compound of formula I increases the solubility of formula I. However, on administration to an animal (including human) plasma phosphatases break the phosphate salt of formula I (formula I-phosphate) down to the parent compound i.e. formula I.

It is evident form FIG. 6 that thirty minutes after administration of formula I-phosphate at 10 mg/kg highlevels of the parent compound were detected in both plasma and tumour. The concentration of formula I decreased with time more rapidly in the plasma than in the tumour and at 24 hr after administration significant levels were detectable in the tumour but none could be detected in the plasma. There was a profound and sustained inhibition of PARP activity in both pbls and tumour: <50% control up to 24 hr.

After administration of formula I-phosphate at 1 mg/kg lower levels of the compound of formula I can be found in both the plasma and tumour and consequently there was a less pronounced effect on PARP activity.

Figure 7:
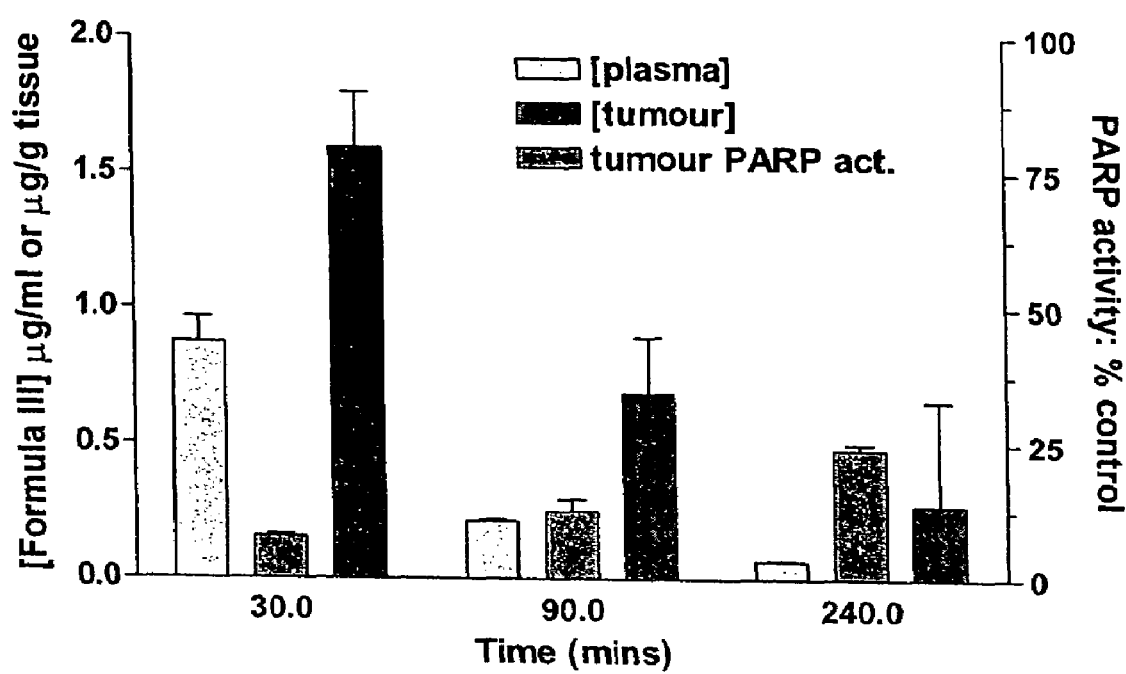
FIG. 7 is a bar chart showing the pharmacokinetics and pharmacodynanics with formula III in mice bearing SW620 xenografts.

FIG. 7 shows the plasma and tumour concentrations of the compound of formula III, and its pharmacokinetic effect on SW620 xenografts (tumour PARP act), at various times following intraperitoneal administration of the 10 mg/kg of compound of formula III. This compound also distributes well to the tumour and is preferentially retained with time and similarly inhibits PARP activity in the tumour.

Figure 8:
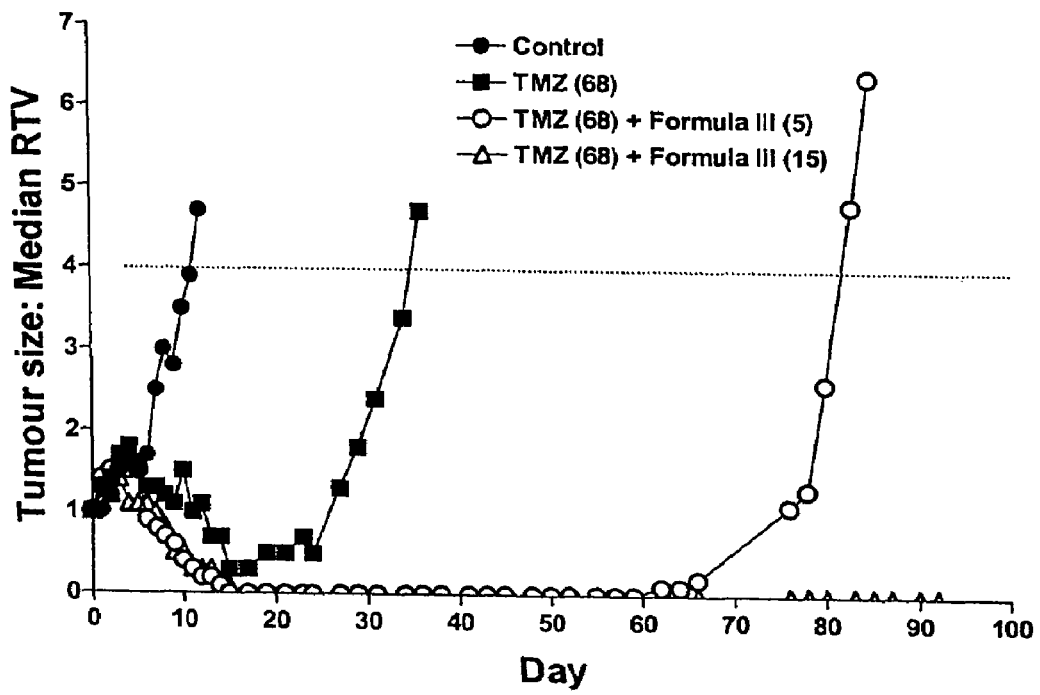
FIG. 8 is a graph showing the tumour growth (median relative tumour volume) in mice bearing SW620 xenografts following treatment with formula III in combination with temozolomide (TMZ) and with TMZ alone.

FIG. 8 shows that for 20 days from administration of temolozomide (68 mg/kg daily×5) the tumour xenograft has progressively reduced in size. However, shortly after this time the tumour size begins to increase. When a compound of formula III (5 mg/kg daily×5) is administered in conjunction with temozolomide the tumour shrinks significantly for around 15 days, to an undetectable size, the tumour size remains undetectable for a further 50 days thereafter when it begins to increase in size. When a larger dose of formula III (15 mg/kg daily×5) is administered the tumour size remains undetectable for a further 80 days until the end of the experiment when no tumour was detectable at autopsy i.e. complete tumour regression.

Figure 9:
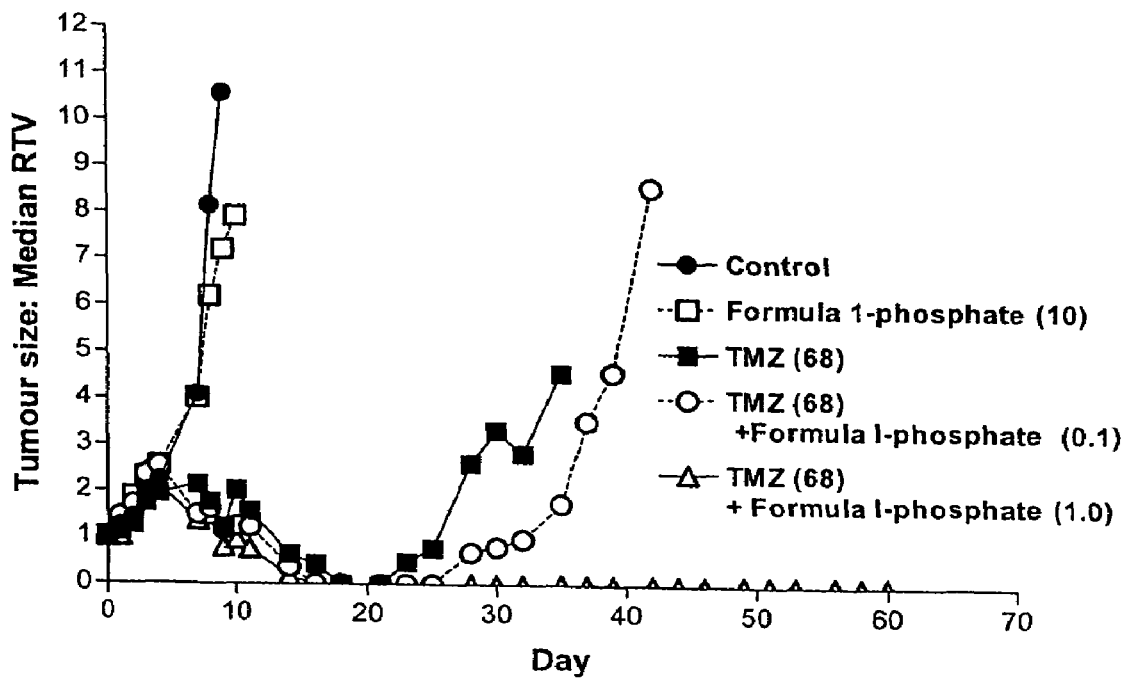
FIG. 9 is a graph showing the tumour growth (median relative tumour volume) of mice bearing SW620 xenografts following treatment with formula I-phosphate in combination with temozolomide (TMZ) and with formula I-phosphate and TMZ alone.

FIG. 9 shows a similar pattern to that seen in FIG. 8 following the administration of formula I-phosphate (at 0.1 mg/kg and 1.0 mg/kg) in combination with temolozomide.

TABLE 1

Genotype and origin of cell lines used in this study.

| Cell line | Genotype | Defect | Origin | Reference | Comments |
|---|---|---|---|---|---|
| AA8 | wt | wt | CHO | [41] | Chinese hamster ovary cell line |
| irs1SF | XRCC3− | XRCC3−, deficient in HR | AA8 | [41] | Radiation-sensitive cell line derived from AA8 which lacks XRCC3 a component of HR pathway |
| CXR3 | XRCC3− + hXRCC3 | wt | irs1SF | [41] | irs1SF transfected with hXRCC3 gene |
| V79-Z | wt | wt | V79 | [42] | V79 are hamster lung fibroblasts |
| VC8 | BRCA2− | BRCA2−, deficient in HR | V79-Z | [42] | VC8 are radiation sensitive derivatives of V79 which are deficient in BRCA2 |
| VC8#13 | BRCA2− + hBRCA2 | wt | VC8 | [42] | VC8 with chromosome 13 containing hBRCA2 |
| VC8 + B2 | BRCA2− + hBRCA2 | wt | VC8 | [42] | VC8 transfected with hBRCA2 |

Materials and Methods

Cytotoxicity of PARP Inhibitors to Cells Deficient in HR (XRCC3 or BRCA2)

Cell Culture

The AA8, irs1SF and CXR3 cell lines were provided by Larry Thompson [41].

The VC-8, VC-8+B2, VC-8#13 were a gift from Malgorzata Zdienicka [42]. All cell lines in this study were grown in Dulbecco's modified Eagle's Medium (DMEM) with 10% Foetalbovine serum and penicillin (100 U/ml) and steptomycin sulphate (100 μg/mL) at 37° C. under an atmosphere containing 5% $CO_2$.

Toxicity Assay—Clonogenic Survival Assay

Figure 1:
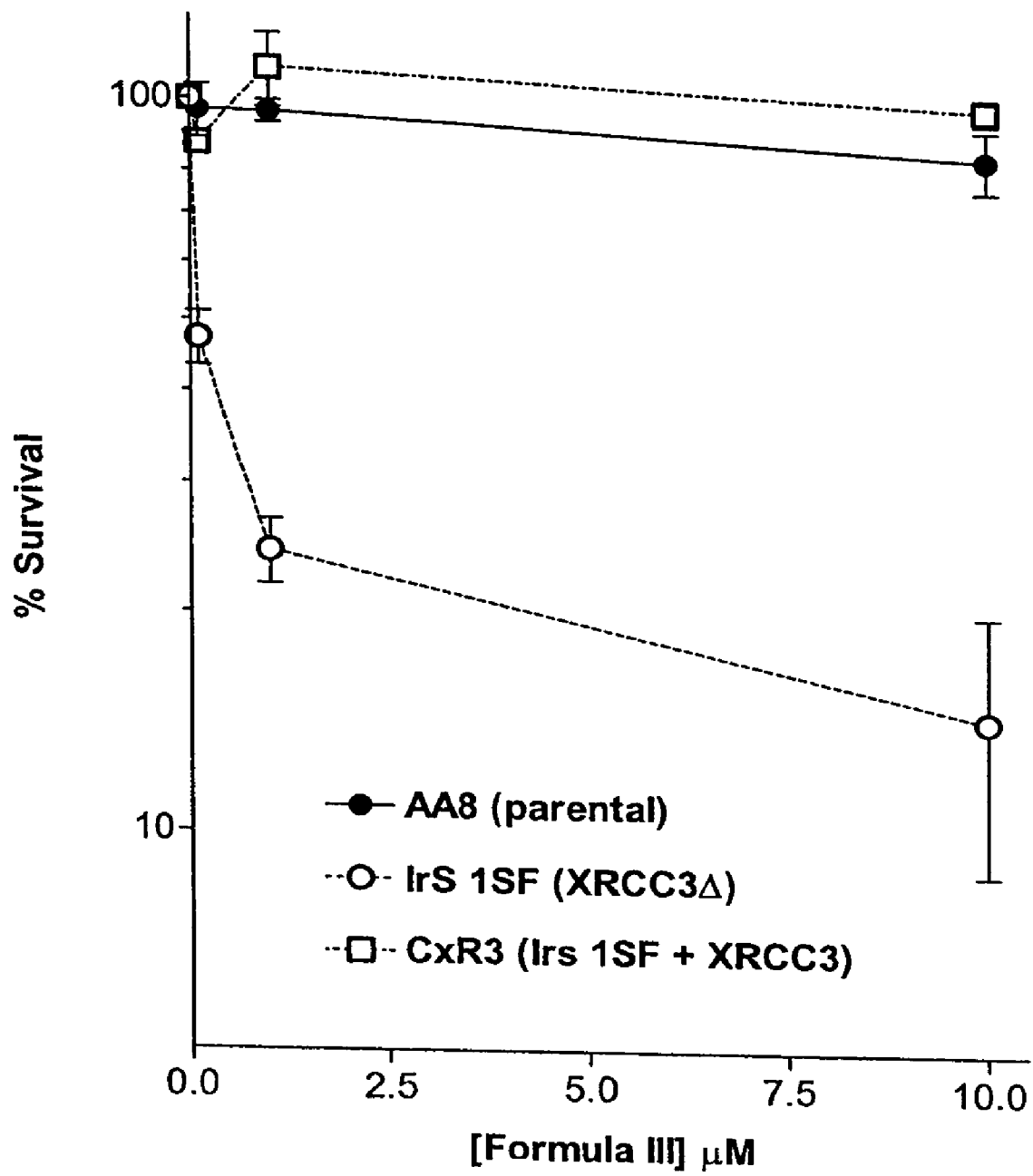
FIG. 1 is a graph showing cell survival in the presence of PARP inhibitor of formula III in AA8 cell line, IsrISF cell line and CxR3 cell line.
Figure 2:
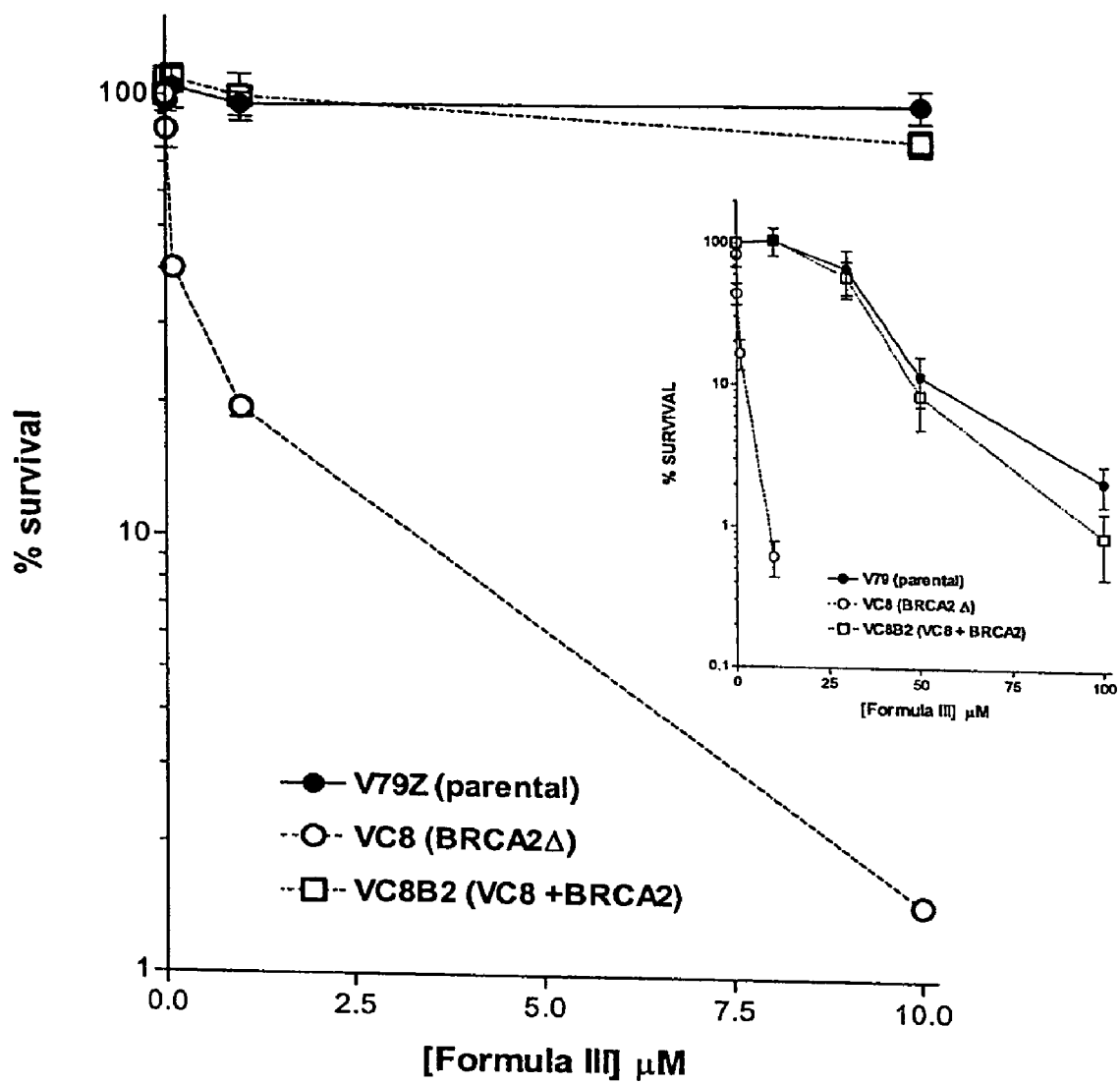
FIG. 2 is a graph showing cell survival in the presence of PARP inhibitor of formula III in V79 cell line, VC8 cell line and VC8B2 cell line.

Exponentially growing cells in 6-well plates were exposed to the compound of formula III at the concentrations indicated in FIG. 2 in 1% DMSO or 1% DMSO alone in medium for 24 hours.

The cells were harvested by trypsinisation, counted and seeded at varying densities in 10 cm dishes in fresh medium in the absence of drug for colony formation.

7-10 days later the dishes were fixed with methanol:acetic acid 3:1 and stained with 0.4% crystal violet.

Colonies were counted and the survival relative to 1% DMSO control treated cells calculated.

PARP Activity Assay

Exponentially growing cells were exposed to 1% DMSO in culture medium (control) or a compound of formula I or III in 1% DMSO at the concentrations indicated in FIG. 4 to cells permeabilised with digitonin, or intact cells for 20 minutes prior to washing and digitonin-permeabilization. PARP activity was measured by incorporation of a [32P] labelled NAD+ substrate into TCA precipitateble polymers after stimulation by the addition of a blunt-ended oligonucleotide and compared with non-oligonucleotide-stimulated cells. PARP activity in tumour homogenates (1 in 40 in isotonic buffer) from formula III-treated mice was measured in the same way. PARP activity in pbls and tumour homogenates from formula I-phospate treated mice was measured by immunological detection of polymer using the 10H antibody. Briefly, tumour homogenates diluted to up to 1:1000 in isotonic buffer were incubated with 350 μM NAD for 6 min and blotted onto nitrocellulose membrane. The poly(ADP-ribose) (PAR) polymer formation was quantified by chemiluminescence detection using a Fuji LAS3000 UV Illuminator by reference to serial dilutions of a PAR standard, following incubation with 10H antibody to PAR and a secondary anti-mouse antibody. The results were standardised by reference to the measured protein content of the homogenate.

It is of course to be understood that the invention is not intended to be restricted to the details of the above embodiments which are described by way of example only.

REFERENCES

[1] C. Lundin, K. Erixon, C. Amaudeau, N. Schultz, D. Jenssen, M. Meuth and T. Helleday Different roles for nonhomologous end joining and homologous recombination following replication arrest in mammalian cells, Mol Cell Biol 22 (2002) 5869-5878.

[2] A. R. Venkitaraman Cancer susceptibility and the functions of BRCA1 and BRCA2, Cell 108 (2002) 171-182.

[3] D. D'Amours, S. Desnoyers, I. D'Silva and G. G. Poirier Poly(ADP-ribosyl)ation reactions in the regulation of nuclear functions, Biochem J 342 (1999) 249-268.

[4] Z. Herceg and Z. Q. Wang Functions of poly(ADP-ribose) polymerase (PARP) in DNA repair, genomic integrity and cell death, Mutat Res 477 (2001) 97-110.

[5] T. Lindahl, M. S. Satoh, G. G. Poirier and A. Klungland Post-translational modification of poly(ADP-ribose) polymerase induced by DNA strand breaks, Trends Biochem Sci 20 (1995) 405-411.

[6] M. S. Satoh and T. Lindahl Role of poly(ADP-ribose) formation in DNA repair, Nature 356 (1992) 356-358.

[7] S. Shall and G. de Murcia Poly(ADP-ribose) polymerase-1: what have we learned from the deficient mouse model?, Mutat Res 460 (2000) 1-15.

[8] Z. Q. Wang, L. Stingl, C. Morrison, M. Jantsch, M. Los, K. Schulze-Osthoff and E. F. Wagner PARP is important for genomic stability but dispensable in apoptosis, Genes Dev 11 (1997) 2347-2358.

[9] C. M. Simbulan-Rosenthal, B. R. Haddad, D. S. Rosenthal, Z. Weaver, A. Coleman, R. Luo, H. M. Young, Z. Q. Wang, T. Ried and M. E. Smulson Chromosomal aberrations in PARP(−/−) mice: genome stabilization in immortalized cells by reintroduction of poly(ADP-ribose) polymerase cDNA, Proc Natl Acad Sci USA 96 (1999) 13191-13196.

[10] J. M. de Murcia, C. Niedergang, C. Trucco, M. Ricoul, B. Dutrillaux, M. Mark, F. J. Oliver, M. Masson, A. Dierich, M. LeMeur, C. Walztinger, P. Chambon and G. de Murcia Requirement of poly(ADP-ribose) polymerase in recovery from DNA damage in mice and in cells, Proc Natl Acad Sci USA 94 (1997) 7303-7307.

[11] F. d'Adda di Fagagna, M. P. Hande, W. M. Tong, P. M. Lansdorp, Z. Q. Wang and S. P. Jackson Functions of poly(ADP-ribose) polymerase in controlling telomere length and chromosomal stability, Nat Genet 23 (1999) 76-80.

[12] E. Samper, F. A. Goytisolo, J. Menissier-de Murcia, E. Gonzalez-Suarez, J. C. Cigudosa, G. de Murcia and M. A. Blasco Normal telomere length and chromosomal end capping in poly(ADP-ribose) polymerase-deficient mice and primary cells despite increased chromosomal instability, J Cell Biol 154 (2001) 49-60.

[13] C. Morrison, G. C. Smith, L. Stingl, S. P. Jackson, E. F. Wagner and Z. Q. Wang Genetic interaction between PARP and DNA-PK in V(D)J recombination and tumorigenesis, Nat Genet 17 (1997) 479-482.

[14] V. Schreiber, D. Hunting, C. Trucco, B. Gowans, D. Grunwald, G. De Murcia and J. M. De Murcia A dominant-negative mutant of human poly(ADP-ribose) polymerase affects cell recovery, apoptosis, and sister chromatid exchange following DNA damage, Proc Natl Acad Sci USA 92 (1995) 4753-4757.

[15] J. H. Kupper, M. Muller and A. Burkle Trans-dominant inhibition of poly(ADP-ribosyl)ation potentiates carcinogen induced gene amplification in SV40-transformed Chinese hamster cells, Cancer Res 56 (1996) 2715-2717.

[16] J. Magnusson and C. Ramel Inhibitor of poly(ADP-ribose)transferase potentiates the recombinogenic but not the mutagenic action of alkylating agents in somatic cells in vivo in Drosophila melanogaster, Mutagenesis 5 (1990) 511-514.

[17] A. S. Waldman and B. C. Waldman Stimulation of intrachromosomal homologous recombination in mammalian cells by an inhibitor of poly(ADP-ribosylation), Nucleic Acids Res 19 (1991) 5943-5947.

[18] A. Semionov, D. Coumoyer and T. Y. Chow Inhibition of poly(ADP-ribose)polymerase stimulates extrachromosomal homologous recombination in mouse Ltk-fibroblasts, Nucleic Acids Res 27 (1999) 4526-4531.

[19] F. Dantzer, V. Schreiber, C. Niedergang, C. Trucco, E. Flatter, G. De La Rubia, J. Oliver, V. Rolli, J. Menissier-de Murcia and G. de Murcia Involvement of poly(ADP-ribose) polymerase in base excision repair, Biochimie 81 (1999) 69-75.

[20] F. Dantzer, G. de La Rubia, J. Menissier-De Murcia, Z. Hostomsky, G. de Murcia and V. Schreiber Base excision repair is impaired in mammalian cells lacking Poly(ADP-ribose) polymerase-1, Biochemistry 39 (2000) 7559-7569.

[21] L. Tentori, I. Portarena and G. Graziani Potential clinical applications of poly(ADP-ribose) polymerase (PARP) inhibitors, Pharmacol Res 45 (2002) 73-85.

[22] T. Lindahl and R. D. Wood Quality control by DNA repair, Science 286 (1999) 1897-1905.

[23] K. W. Caldecott DNA single-strand break repair and spinocerebellar ataxia, Cell 112 (2003) 7-10.

[24] D. D'Amours and S. P. Jackson The Mre11 complex: at the crossroads of dna repair and checkpoint signalling, Nat Rev Mol Cell Biol 3 (2002) 317-327.

[25] A. D. D'Andrea and M. Grompe The Fanconi anaemia/BRCA pathway, Nat Rev Cancer 3 (2003) 23-34.

[26] S. P. Jackson Sensing and repairing DNA double-strand breaks, Carcinogenesis 23 (2002) 687-696.

[27] R. Kanaar, J. H. Hoeijmakers and D. C. van Gent Molecular mechanisms of DNA double strand break repair, Trends Cell Biol 8 (1998) 483-489.

[28] D. C. van Gent, J. H. Hoeijmakers and R. Kanaar Chromosomal stability and the DNA double-stranded break connection, Nat Rev Genet 2 (2001) 196-206.

[29] S. L. Neuhausen and E. A. Ostrander Mutation testing of early-onset breast cancer genes BRCA1 and BRCA2, Genet Test 1 (1997) 75-83.

[30] G. Kuperstein, W. D. Foulkes, P. Ghadirian, J. Hakimi and S. A. Narod A rapid fluorescent multiplexed-PCR analysis (FMPA) for founder mutations in the BRCA1 and BRCA2 genes, Clin Genet 57 (2000) 213-220.

[31] Vissac-Sabatier C, Coxam V, Dechelotte P, Picherit C, Horcajada M-N, Davicco M-J, Lebecque P, Bignon Y-J, and Bemard-Gallon D. Phytoestrogen-rich diets modulate expression of BRCA1 and BRCA2 tumour suppressor genes in mammary glands of female Wistar rats. Cancer Research vol 63 pp 6607-6612 (2003).

[32] Wu K, Jiang S-W and Couch F J. p53 mediates repression of the BRCA2 promoter and down regulation of BRCA2 mRNA and protein levels in response to DNA damage. J. Biol. Chem. Vol 278 pp 15652-15660 (2003).

[33] A. Chiarugi Poly(ADP-ribose) polymerase: killer or conspirator? The 'suicide hypothesis' revisited, Trends Phamacol Sci 23 (2002) 122-129.

[34] C. R. Calabrese, M. A. Batey, H. D. Thomas, B. W. Durkacz, L. Z. Wang, S. Kyle, D. Skalitzky, J. Li, C. Zhang, T. Boritzki, K. Maegley, A. H. Calvert, Z. Hostomsky, D. R. Newell and N. J. Curtin Identification of Potent Nontoxic Poly(ADP-Ribose) Polymerase-1 Inhibitors: Chemopotentiation and Pharmacological Studies, Clin Cancer Res 9 (2003) 2711-2718.

[35] D. Ferraris, Y. S. Ko, T. Pahutski, R. P. Ficco, L. Serdyuk, C. Alemu, C. Bradford, T. Chiou, R. Hoover, S. Huang, S. Lautar, S. Liang, Q. Lin, M. X. Lu, M. Mooney, L. Morgan, Y. Qian, S. Tran, L. R. Williams, Q. Y. Wu, J. Zhang, Y. Zou and V. Kalish Design and synthesis of poly ADP-ribose polymerase-1 inhibitors. 2. Biological evaluation of aza-5[H]-phenanthridin-6-ones as potent, aqueous-soluble compounds for the treatment of ischemic injuries, J Med Chem 46 (2003) 3138-3151.

[36] K. J. Dillon, G. C. Smith and N. M. Martin A FlashPlate assay for the identification of PARP-1 inhibitors, J Biomol Screen 8 (2003) 347-352.

[37] A. J. Pierce, R. D. Johnson, L. H. Thompson and M. Jasin XRCC3 promotes homology-directed repair of DNA damage in mammalian cells, Genes Dev 13 (1999) 2633-2638.

[38] R. D. Johnson, N. Liu and M. Jasin Mammalian XRCC2 promotes the repair of DNA double-strand breaks by homologous recombination, Nature 401 (1999) 397-399.

[39] G. M. Shah, D. Poirier, S. Desnoyers, S. Saint-Martin, J. C. Hoflack, P. Rong, M. ApSimon, J. B. Kirkland and G. G. Poirier Complete inhibition of poly(ADP-ribose) polymerase activity prevents the recovery of C3H10T1/2 cells from oxidative stress, Biochim Biophys Acta 1312 (1996) 1-7.

[40] R. J. Griffin, S. Srinivasan, K. Bowman, A. H. Calvert, N. J. Curtin, D. R. Newell, L. C. Pemberton and B. T. Golding Resistance-modifying agents. 5. Synthesis and biological properties of quinazolinone inhibitors of the DNA repair enzyme poly(ADP-ribose) polymerase (PARP), J Med Chem 41 (1998) 5247-5256.

[41] S. Boulton, L. C. Pemberton, J. K. Porteous, N. J. Curtin, R. J. Griffin, B. T. Golding and B. W. Durkacz Potentiation of temozolomide-induced cytotoxicity: a comparative study of the biological effects of poly(ADP-ribose) polymerase inhibitors, Br J Cancer 72 (1995) 849-856.

[42] C. S. Griffin, P. J. Simpson, C. R. Wilson and J. Thacker Mammalian recombination-repair genes XRCC2 and XRCC3 promote correct chromosome segregation, Nat Cell Biol 2 (2000) 757-761.

[43] R. S. Tebbs, Y. Zhao, J. D. Tucker, J. B. Scheerer, M. J. Siciliano, M. Hwang, N. Liu, R. J. Legerski and L. H. Thompson Correction of chromosomal instability and sensitivity to diverse mutagens by a cloned cDNA of the XRCC3 DNA repair gene, Proc Natl Acad Sci USA 92 (1995) 6354-6358.

[44] M. Kraakman-van der Zwet, W. J. Overkamp, R. E. van Lange, J. Essers, A. van Duijn-Goedhart, I. Wiggers, S. Swaminathan, P. P. van Buul, A. Errami, R. T. Tan, N. G. Jaspers, S. K. Sharan, R. Kanaar and M. Z. Zdzienicka Brca2 (XRCC11) deficiency results in radioresistant DNA synthesis and a higher frequency of spontaneous deletions, Mol Cell Biol 22 (2002) 669-679.

The invention claimed is:

1. A method for treating cancer in a mammal, wherein the cancer is caused by a genetic defect in a gene that mediates homologous recombination, wherein the gene is at least one of BRCA1 and BRCA2, the method comprising:
   selecting the mammal having the genetic defect; and
   administering to the mammal a compound selected from the group consisting of a compound of the formula I, formula II and formula III:

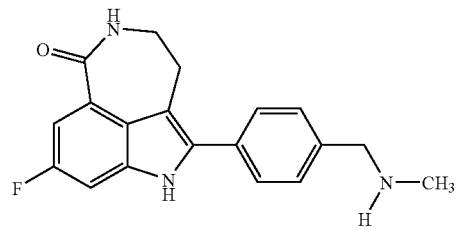

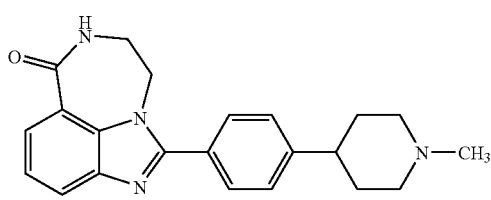

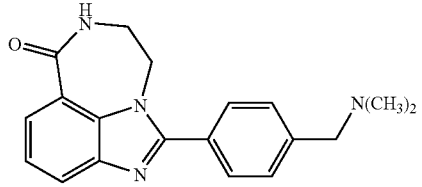

or a pharmaceutically acceptable salt thereof,
   wherein the compound is used as a direct cytotoxic agent.

2. The method according to claim 1, wherein the compound is the compound of the formula I.

3. The method according to claim 2, wherein the compound of the formula I is in the form of a phosphate salt.

4. The method of claim 1, wherein the cancer is breast cancer.

5. The method of claim 1, wherein the genetic defect is the absence of BRCA1 and/or BRCA2.

6. The method of claim 1, wherein the genetic defect is in the expression of BRCA1 and/or BRCA2.

* * * * *

UNITED STATES PATENT AND TRADEMARK OFFICE
CERTIFICATE OF CORRECTION

| | |
|---|---|
| PATENT NO. | : 7,351,701 B2 |
| APPLICATION NO. | : 10/898653 |
| DATED | : April 1, 2008 |
| INVENTOR(S) | : Helleday et al. |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (412) days Delete the phrase "by 62" and insert -- by 0 days --

Signed and Sealed this

Nineteenth Day of May, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,351,701 B2
APPLICATION NO. : 10/898653
DATED : April 1, 2008
INVENTOR(S) : Helleday et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (62) days Delete the phrase "by 62" and insert -- by 0 days --

This certificate supersedes the Certificate of Correction issued May 19, 2009.

Signed and Sealed this

Fourth Day of August, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,351,701 B2
APPLICATION NO. : 10/898653
DATED : April 1, 2008
INVENTOR(S) : Curtin It is certified that error appears in the above-identified patent and that said Letters Patent is hereby corrected as shown below:

On the Title Page

Item (12), should read: Curtin

Item (72), delete: "Thomas Helleday, Stockholm (SE)"

Signed and Sealed this
Tenth Day of September, 2024

Katherine Kelly Vidal
*Director of the United States Patent and Trademark Office*